US010827771B2

(12) United States Patent
Kondo et al.

(10) Patent No.: US 10,827,771 B2
(45) Date of Patent: Nov. 10, 2020

(54) METHOD FOR PRODUCING YEAST EXTRACT, YEAST EXTRACT OBTAINED THEREBY, SEASONING COMPOSITION, AND FOOD

(71) Applicant: TABLEMARK CO., LTD., Tokyo (JP)

(72) Inventors: Atsushi Kondo, Tokyo (JP); Junko Tanizawa, Tokyo (JP)

(73) Assignee: TABLEMARK CO., LTD., Tokyo (JP)

( * ) Notice: Subject to any disclaimer, the term of this patent is extended or adjusted under 35 U.S.C. 154(b) by 141 days.

(21) Appl. No.: 15/569,976

(22) PCT Filed: Apr. 27, 2016

(86) PCT No.: PCT/JP2016/063165
§ 371 (c)(1),
(2) Date: Oct. 27, 2017

(87) PCT Pub. No.: WO2016/175235
PCT Pub. Date: Nov. 3, 2016

(65) Prior Publication Data
US 2019/0045820 A1 Feb. 14, 2019

(30) Foreign Application Priority Data
Apr. 28, 2015 (JP) ................................ 2015-091617

(51) Int. Cl.
| | | |
|---|---|---|
| *A23L 23/10* | (2016.01) | |
| *A23L 27/10* | (2016.01) | |
| *A23L 27/22* | (2016.01) | |
| *A23L 31/15* | (2016.01) | |
| *C12P 7/56* | (2006.01) | |
| *A23L 27/20* | (2016.01) | |
| *C12P 1/02* | (2006.01) | |
| *A23L 33/10* | (2016.01) | |
| *C12P 7/46* | (2006.01) | |
| *C12P 7/54* | (2006.01) | |
| *A23L 33/145* | (2016.01) | |
| *A23L 27/24* | (2016.01) | |
| *A23L 17/00* | (2016.01) | |

(52) U.S. Cl.
CPC .............. *A23L 27/10* (2016.08); *A23L 17/00* (2016.08); *A23L 27/20* (2016.08); *A23L 27/2028* (2016.08); *A23L 27/22* (2016.08); *A23L 27/24* (2016.08); *A23L 31/15* (2016.08); *A23L 33/10* (2016.08); *A23L 33/145* (2016.08); *C12P 1/02* (2013.01); *C12P 7/46* (2013.01); *C12P 7/54* (2013.01); *C12P 7/56* (2013.01); *A23V 2002/00* (2013.01)

(58) Field of Classification Search
CPC .......... A23L 17/00; A23L 27/10; A23L 27/20; A23L 27/2028; A23L 27/21; A23L 27/22; A23L 27/24; A23L 31/15; A23L 33/10; A23L 33/14; A23L 33/145; C12P 1/02; C12P 7/46; C12P 7/54; C12P 7/56

USPC ......................................................... 426/643
See application file for complete search history.

(56) References Cited

U.S. PATENT DOCUMENTS

| | | |
|---|---|---|
| 5,288,509 A | 2/1994 | Potman et al. |
| 2011/0223287 A1 | 9/2011 | Shibuya et al. |

FOREIGN PATENT DOCUMENTS

| | | | |
|---|---|---|---|
| CN | 102216442 A | | 10/2011 |
| EP | 0249435 A2 | | 12/1987 |
| JP | 9-294581 A | | 11/1997 |
| JP | 9-313169 A | | 12/1997 |
| JP | 10-327802 A | | 12/1998 |
| JP | 2002-171961 A | | 6/2002 |
| JP | 2005102549 A | * | 4/2005 |
| JP | 2006-129835 A | | 5/2006 |
| JP | 2009-261253 A | | 11/2009 |
| JP | 4398213 B2 | * | 1/2010 |
| JP | 2010-148517 A | | 7/2010 |
| WO | WO 02/068612 A1 | | 9/2002 |
| WO | WO 2012/067106 A1 | | 5/2012 |
| WO | WO-2012067106 A1 | * | 5/2012 |

OTHER PUBLICATIONS

Australian Office Action dated Oct. 8, 2019, for corresponding Australian Patent Application No. 2016253885.
International Preliminary Report on Patentability and Written Opinion of the International Searching Authority (Forms PCT/IB/373 and PCT/ISA/237) for Application No. PCT/JP2016/063165, dated Oct. 31, 2017, with an English translation.
International Search Report and English translation (Form PCT/ISA/210) for Application No. PCT/JP2016/063165, dated Jun. 7, 2016.
Extended European Search Report, dated Oct. 9, 2018, for corresponding European Application No. 16786511.2.
European Office Action dated May 13, 2020, for corresponding European Patent Application No. 16 786 511.2.
Japanese Office Action dated Apr. 21, 2020, for corresponding Japanese Patent Application No. 2017-515572, with an English translation.

(Continued)

*Primary Examiner* — Jyoti Chawla
(74) *Attorney, Agent, or Firm* — Birch, Stewart, Kolasch & Birch, LLP

(57) ABSTRACT

There is provided a method for producing a yeast extract containing an organic acid, especially succinic acid, at a high concentration, and further containing glutamic acid at a high concentration. There is provided such a production method comprising an organic acid generation treatment step of maintaining a suspension of cultured yeast under conditions effective for organic acid generation to increase organic acid content in the yeast; and a hot water extraction step of extracting a yeast extract from the yeast that has undergone the organic acid generation treatment step at 56° C. or higher.

6 Claims, 3 Drawing Sheets

(56) References Cited

OTHER PUBLICATIONS

Chinese Office Action and Search Report for corresponding Chinese Application No. 201680024604.7, dated Jul. 1, 2020, with an English translation.

* cited by examiner

[Fig. 1]
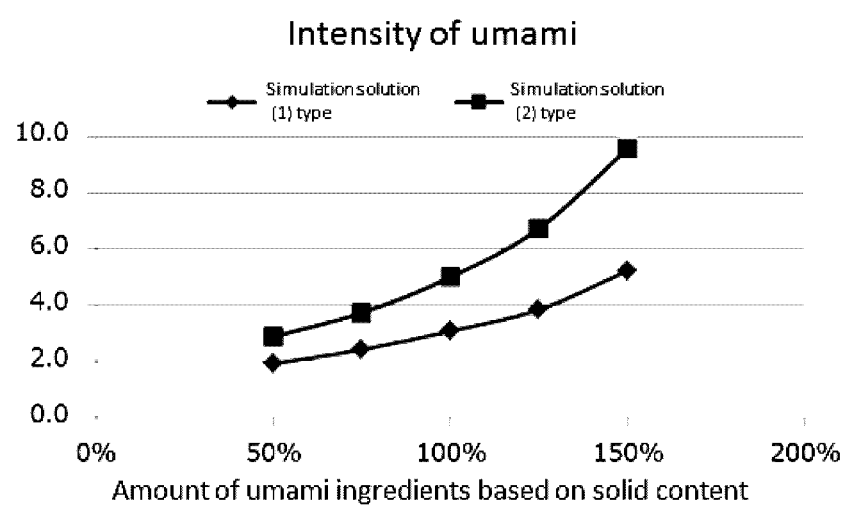

[Fig. 2]
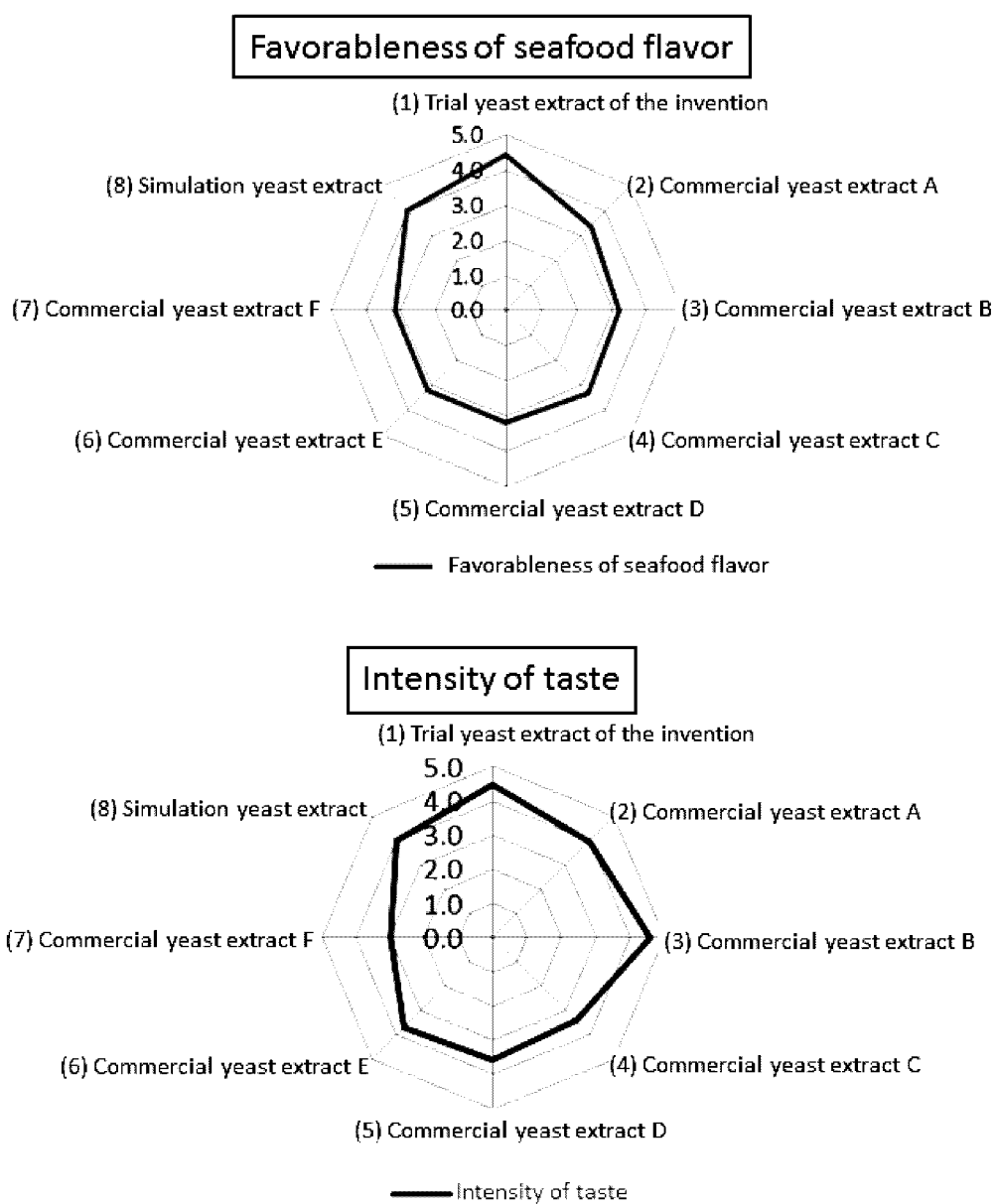

[Fig. 3]
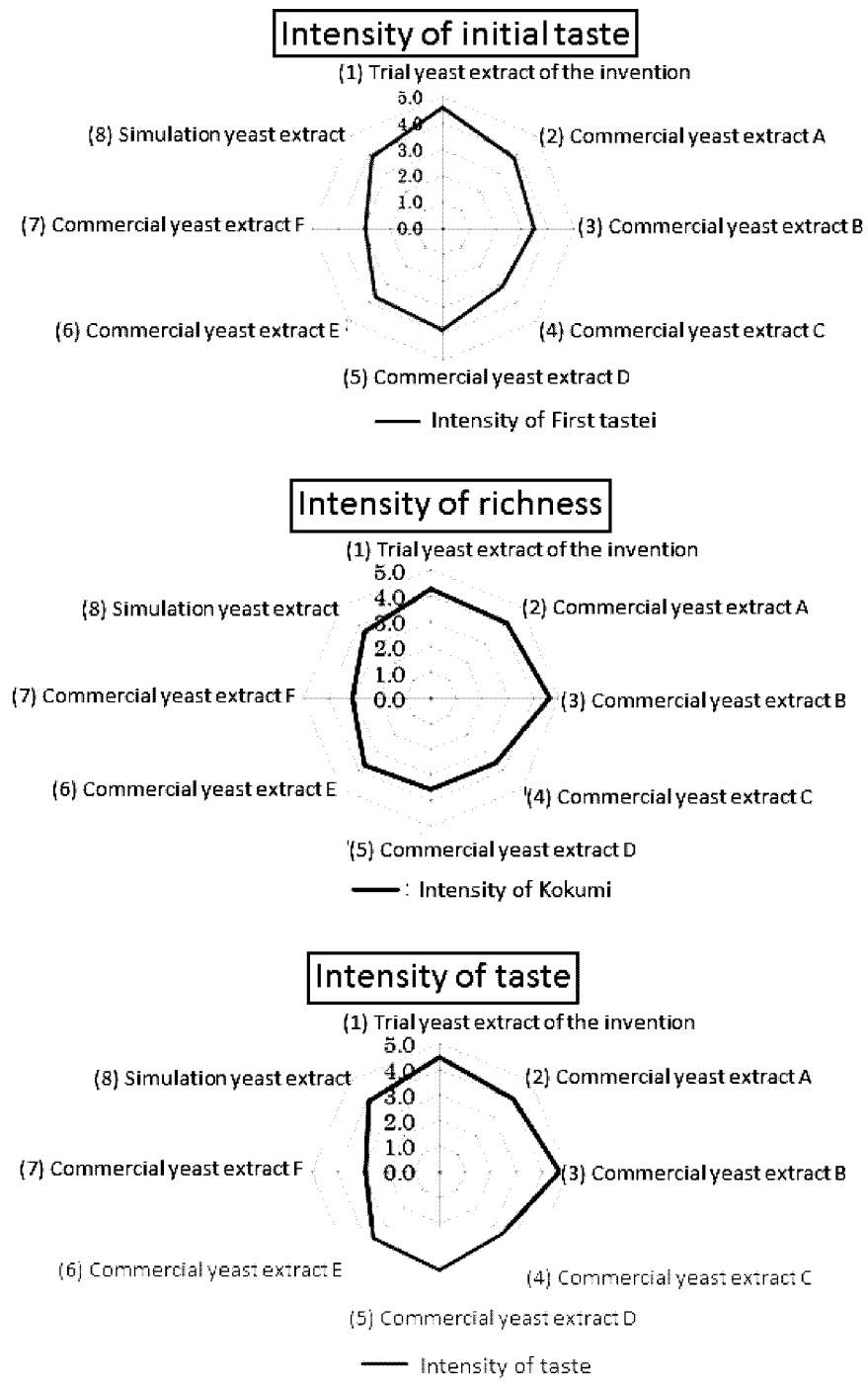

METHOD FOR PRODUCING YEAST EXTRACT, YEAST EXTRACT OBTAINED THEREBY, SEASONING COMPOSITION, AND FOOD

TECHNICAL FIELD

The present invention relates to a novel method for producing a yeast extract. More precisely, the present invention relates to a method for producing a succinic acid- and glutamic acid-enriched yeast extract. The present invention is useful in the field of food manufacturing, and so forth.

BACKGROUND ART

Typical umami ingredients of foods include taste nucleic acids, glutamic acid or sodium glutamate, and organic acids such as succinic acid. Taste nucleic acids are known as umami ingredients of dried bonito or shiitake mushroom, and are used in the form of monosodium inosinate or monosodium guanylate. Glutamic acid or sodium glutamate is known as a taste ingredient of kelp stock, and succinic acid is known as a taste ingredient of shellfish. Further, mineral salts of lactic acid or acetic acid are also used for foods as seasonings for the purpose of obtaining good harmony of flavors.

Such umami ingredients as described above are conventionally produced by chemical synthesis or microbial fermentation, and have been used as ingredients called chemical seasonings. However, in recent years, with the rise of nature-oriented mind of consumers, there is increasing consumption of yeast extracts instead of artificial seasonings regarded as food additives. Since yeast extracts contain many ingredients produced by yeasts, yeast extracts have characteristic complicated taste and aroma. It has been becoming clear that yeast extracts have enhancing effect, masking effect, and so forth for specific taste or aroma, and use thereof for foods for various purposes is investigated.

It is well known that taste nucleic acids and glutamic acid or sodium glutamate synergistically enhance umami. As also for yeast extracts, various yeast extracts containing glutamic acid or sodium glutamate alone or together with nucleic acid have been investigated (Patent documents 1 to 7). As for succinic acid, for example, Patent document 8 discloses a yeast extract, as a yeast extract that can enhance not only the original thickness and complicated tastes of dashi stock, but also testes of the whole stock with good balance, and also appropriately enhance umami, which is obtained by digesting or decomposing yeast cells, and in which, among peptides detected by absorption photometry at 220 nm in a gel filtration filtrate obtained by filtering the yeast extract through a filtration membrane having pores of 1 micrometer in diameter, and subjecting the filtrate to gel filtration, ratio of peptides having a molecular weight of 10000 or higher is 10% or higher based on the total peptides. It is described that, according to a preferred embodiment of this yeast extract, the yeast extract contains 10% or more of sodium glutamate based on the solid content, and 0.6% or more of succinic acid based on the solid content. Further, Patent document 9 proposes a method for producing a yeast extract containing succinic acid at a higher concentration compared with conventional products by autolysis, in which a yeast extract is extracted from yeast cells cultured under conditions that KLa (volumetric oxygen transfer rate) is 0.9 to 195 $hr^{-1}$.

PRIOR ART REFERENCES

Patent Documents

Patent document 1: Japanese Patent Unexamined Publication (KOKAI) No. 09-294581
Patent document 2: Japanese Patent Unexamined Publication (KOKAI) No. 09-313169
Patent document 3: Japanese Patent Unexamined Publication (KOKAI) No. 10-327802
Patent document 4: Japanese Patent Unexamined Publication (KOKAI) No. 2002-171961
Patent document 5: Japanese Patent Unexamined Publication (KOKAI) No. 2006-129835
Patent document 6: Japanese Patent Unexamined Publication (KOKAI) No. 2009-261253
Patent document 7: Japanese Patent Unexamined Publication (KOKAI) No. 2010-148517
Patent document 8: Japanese Patent No. 4398213
Patent document 9: International Patent Publication WO2012/067106A1

SUMMARY OF THE INVENTION

Object to be Achieved by the Invention

As for taste nucleic acids and sodium glutamate among the umami ingredients, yeast extracts containing large amounts of them have already been commercially produced and distributed. However, as for succinic acid, the content thereof in the existing yeast extract products is about 1.8% even in those having the highest succinic acid content. Further, although Patent document 8 mentioned above discloses a yeast extract containing 10% or more of sodium glutamate and 0.6% or more of succinic acid, it cannot be said that the succinic acid content thereof is particularly high.

Further, there is not yet known any method for producing a yeast extract containing both glutamic acid or sodium glutamate and succinic acid at high concentrations. Although Patent document 9 mentioned above discloses a method for producing a yeast extract containing 3.0 to 30.0% of succinic acid based on dry weight of the yeast extract, it does not refer to sodium glutamate content. In addition, the culture of yeast under the conditions that KLa is 0.9 to 195 $hr^{-1}$ is indispensable for the production method of Patent document 9, but under such conditions, proliferation rate of yeast is extremely slow, and therefore it is expected that the method is not suitable for commercial production.

An object of the present invention is to provide a practical method for producing a yeast extract containing an organic acid, especially succinic acid, at a high concentration. The object of the present invention is to provide, as a preferred embodiment, a method for producing a yeast extract containing succinic acid at a high concentration and also containing glutamic acid at a high concentration.

Means for Achieving the Object

The inventors of the present invention conducted various researches in order to achieve the aforementioned object. As a result, they found that amount of a specific organic acid such as succinic acid in yeasts can be increased or decreased by proliferating yeasts under aerobic conditions, and then maintaining the obtained yeast suspension under predetermined conditions, and thus accomplished the present invention.

Further, the inventors of the present invention bred yeasts having a high glutamic acid-producing ability and developed yeast extracts of high glutamic acid content. Therefore, they conducted various researches by using such yeasts in order to increase succinic acid content and also increase glutamic acid content in yeasts under predetermined conditions. As a result, they found that a yeast extract containing both succinic acid and glutamic acid at high concentrations can be obtained, and accomplished the present invention.

The present invention thus provides the followings:

[1] A method for producing a yeast extract, which comprises:

an organic acid generation treatment step of maintaining a suspension of cultured yeast under conditions effective for organic acid generation to increase organic acid content in the yeast; and a hot water extraction step of extracting a yeast extract from the yeast that has undergone the organic acid generation treatment step with hot water.

[2] The method according to 1, wherein the yeast extract is extracted with hot water at 56° C. or higher in the hot water extraction step.

[3] The method according to 1 or 2, wherein the conditions effective for organic acid generation include maintaining the suspension of yeast for 2 to 30 hours with stirring the suspension.

[4] The method according to any one of 1 to 3, wherein the conditions effective for organic acid generation include maintaining the suspension of yeast at 40 to 55° C. and pH 4.0 to 7.5.

[5] The method according to any one of 1 to 4, wherein the cultured yeast to be subjected to the organic acid generation treatment has been cultured under such conditions that the volumetric oxygen transfer rate (KLa) is 500 hr$^{-1}$ or higher.

[6] The method according to any one of 1 to 5, wherein amount of nitrogen contained in the cultured yeast to be subjected to the organic acid generation treatment at the end of the culture is 8.5% or lower based on dry weight of the yeast.

[7] The method according to any one of 1 to 6, wherein the organic acid is selected from the group consisting of succinic acid, lactic acid, and acetic acid.

[8] The method according to any one of 1 to 7, wherein the conditions effective for organic acid generation also increase glutamic acid content of the yeast.

[9] The method according to any one of 1 to 8, wherein the yeast belongs to the genus *Saccharomyces* or *Candida*.

[10] The method according to any one of 1 to 9, wherein the yeast is a highly glutamic acid-producing yeast.

[11] A yeast extract produced by the method according to any one of 1 to 9, wherein:

the yeast belongs to the genus *Saccharomyces*, and the yeast extract contains 5.0% by weight or more of succinic acid and 10.0% by weight or more of glutamic acid based on dry weight of the yeast extract, or the yeast belongs to the genus *Candida*, and the yeast extract contains 2.0% by weight or more of succinic acid and 6.0% by weight or more of glutamic acid based on dry weight of the yeast extract.

[12] A seasoning composition for improving any one selected from the group consisting of initial taste, richness, and taste of a food, which contains a yeast extract containing 5.0% by weight or more of succinic acid and 10.0% by weight or more of glutamic acid based on dry weight of the yeast extract.

[13] A seasoning composition for improving seafood flavor or taste of a food of which raw material contains seafood, which contain a yeast extract containing 5.0% by weight or more of succinic acid and 10.0% by weight or more of glutamic acid based on dry weight of the yeast extract.

[14] A method for producing a food, which comprises the step of adding a yeast extract containing 5.0% by weight or more of succinic acid and 10.0% by weight or more of glutamic acid based on dry weight of the yeast extract to a food to obtain a food of which any one selected from the group consisting of initial taste, richness, and taste is improved.

[15] A method for producing a food, which comprises the step of adding a yeast extract containing 5.0% by weight or more of succinic acid and 10.0% by weight or more of glutamic acid based on dry weight of the yeast extract to a food of which raw material contains seafood to obtain a food of which seafood flavor or taste is improved.

Effect of the Invention

The present invention provides a method for producing a yeast extract containing an organic acid, especially succinic acid, at a high concentration.

According to a preferred embodiment of the present invention, there is provided a method for producing a yeast extract containing both succinic acid and glutamic acid at high concentrations.

The obtained yeast extract containing succinic acid and glutamic acid at high concentrations can improve flavors of seafood in foods, and can enhance tastes by synergistic actions of various contained amino acids and organic acids.

The method for producing a yeast extract provided by the present invention enables commercial production of a yeast extract containing succinic acid at a high concentration, or according to a preferred embodiment, both succinic acid and glutamic acid at high concentrations.

BRIEF DESCRIPTION OF THE DRAWINGS

FIG. 1 Comparison of umami intensity. Umami intensities of a solution containing a glutamic acid and taste nucleic acid (simulation solution (1)) and a solution corresponding to the foregoing solution further containing an organic acid (simulation solution (2)) were compared.

FIG. 2 Taste-improving effect of yeast extract. To a seafood stock, each of the yeast extracts of (1) to (8) and simulation solution in which umami ingredients in yeast extract were reconstructed with reagents was added in an amount of 0.01% (dry weight of yeast extract) at the time of eating or such an amount that umami ingredient concentrations corresponding to those of yeast extract were obtained, and the obtained mixtures were evaluated for favorableness of seafood flavor and intensity of taste.

FIG. 3 Taste-improving effect of yeast extract. To a chicken soup, each of the yeast extracts of (1) to (8) and simulation solutions in which umami ingredients in yeast extract were reconstructed with reagents was added in an amount of 0.05% (dry weight of yeast extract) at the time of eating or such an amount that umami ingredient concentrations corresponding to those of yeast extract were obtained, and the obtained mixtures were evaluated.

MODES FOR CARRYING OUT THE INVENTION

The numerical value ranges indicated as "X to Y" include values of X and Y as the maximum and minimum values, unless especially indicated. The symbol % or the term part are used on the weight basis, unless especially indicated. The expression "A or B" means at least one of A and B, or both A and B, unless especially indicated. Contents (weight %) of ingredients in yeast suspensions are indicated in terms of a value based on dry weight of yeast cells, unless especially indicated. Contents (weight %) of ingredients in yeast extracts are indicated in terms of a value based on dry weight of yeast extract (also referred to as "solid content"), unless especially indicated.

The term "yeast extract" means ingredients extracted from yeast, unless especially indicated, and usually contains organic acids, amino acids, peptides, nucleic acids, minerals, and so forth. Form of the yeast extract is not particularly limited, and it may be in the form of concentrate, partially purified crude product, liquid, dry substance, powder, granule, or the like.

Glutamic acid as an ingredient of yeast or yeast extract may be in the form of salt or solvate of glutamic acid such as sodium glutamate (also referred to as monosodium glutamate, MSG, or soda glutamate), unless especially indicated. The term nucleic acid as an ingredient of yeast or yeast extract means a taste nucleic acid showing umami unless especially indicated, and it may be 5'-inosinic acid, 5'-guanylic acid, 5'-adenylic acid, 5'-uracilic acid, 5'-cytidylic acid, a metal salt thereof, or a solvate thereof (for example, heptahydrate of disodium salt). The term amino acid as ingredient of yeast or yeast extract is an L-amino acid, unless especially indicated.

The food may be a solid food, or may be an orally ingestible liquid product such as drink or soup. The food may be a food that is ingested as it is (for example, various kinds of precooked foods, supplements, drinkable preparations), or may be a food additive, seasoning composition, or drinkable concentrate. The food may be a food for humans, or may be a food for nonhuman animals (pets, livestock, etc.). The food may be a common food (it may be so-called health food), or may be a food with health claims (it may be a food with nutrient function claims or food with health claims).

Hereafter, the present invention will be explained in detail.

The present invention provides a method for producing a yeast extract. The method of the present invention comprises the following steps:

an organic acid generation treatment step of maintaining a suspension of cultured yeast under conditions effective for organic acid generation to increase organic acid content in the yeast; and a hot water extraction step of extracting a yeast extract from the yeast that has undergone the organic acid generation treatment step with hot water.

[Yeast]

The yeast to be used is not particularly limited, so long as a yeast usually used in the field of food manufacturing is chosen. Yeasts belonging to a genus selected from the group consisting of the genera *Saccharomyces, Schizosaccharomyces, Pichia, Candida, Kluyveromyces, Williopsis, Debaryomyces, Galactomyces, Torulasupora, Rhodotorula, Yarrowia*, and *Zygosaccharomyces* can be used. The yeast is preferably a baker's yeast used for bread manufacturing, torula yeast used for manufacturing foods, feeds, and so forth, or brewer's yeast used for beer manufacturing, since they show favorable proliferation, and the yeast is more preferably a yeast belonging to the genus *Saccharomyces* or yeast belonging to the genus *Candida*. Examples of the yeast belonging to the genus *Saccharomyces* include *Saccharomyces cerevisiae*. Examples of the yeast belonging to the genus *Candida* include *Candida tropicalis, Candida lipolytica, Candida utilis*, and *Candida sake*. Preferred examples are yeast strains of *Saccharomyces cerevisiae*, or *Candida utilis*.

More preferred examples are glutamic acid-rich yeast and nucleic acid-rich yeast, and a further preferred example is glutamic acid-rich yeast. Examples of glutamic acid-rich yeast include the *Saccharomyces cerevisiae* FT4 strain. In a particularly preferred embodiment, a strain obtained by citric acid resistance screening of glutamic acid-rich yeasts can be used. Citric acid resistance screening of glutamic acid-rich yeasts can be performed by, for example, culturing glutamic acid-rich yeasts or mutant strains thereof at a temperature around the optimum temperature for 3 to 7 days in a medium containing 50 to 100 mM citric acid, and selecting a strain showing high proliferation rate. By measuring objective organic acid contents or glutamic acid contents of the obtained strains, a strain containing the organic acid or glutamic acid at a high concentration may be further selected if such further selection is appropriate. Examples of strain obtained by citric acid resistance screening of glutamic acid-rich yeasts include the *Saccharomyces cerevisiae* SC21 strain.

The *Saccharomyces cerevisiae* FT4 strain was deposited at the independent administrative agency, National Institute of Advanced Industrial Science and Technology (address: Tsukuba Central 6, 1-1-1, Higashi, Tsukuba-shi, Ibaraki, Japan) on Jun. 20, 2002 by Japan Tobacco, Inc. (address: 2-2-1, Toranomon, Minato-ku, Tokyo, Japan), and assigned an accession number of FERM BP-8081. The *Saccharomyces cerevisiae* SC21 strain was deposited at the independent administrative agency, National Institute of Technology and Evaluation, Patent Microorganisms Depository (address: #122, 2-5-8 Kazusakamatari, Kisarazu, Chiba, Japan) on Mar. 6, 2015 by Atsushi Kondo (address: c/o TableMark Co., Ltd., Food Development Center, 5-14, Hanedaasahi-cho, Ota-ku, Tokyo, Japan), and assigned an accession number of NITE BP-02025. The depositor's name was then changed from Atsushi Kondo to TableMark Co., Ltd. (address: 6-4-10, Tsukiji, Chuo-ku, Tokyo, Japan). From April 2012, the business of the independent administrative agency, National Institute of Advanced Industrial Science and Technology was succeeded by the National Institute of Technology and Evaluation, Biotechnology Center, International Patent Organism Depository (NITE-IPOD) (address from April 2013: #120, 2-5-8 Kazusakamatari, Kisarazu, Chiba, Japan). The independent administrative agency, National Institute of Advanced Industrial Science and Technology was reorganized as the national research and development agency, National Institute of Advanced Industrial Science and Technology in April 2015.

[Culture]

The yeast is cultured in advance of the organic acid generation treatment explained later. The culture is preferably performed under aerobic conditions. It is because, if the culture is performed under such conditions, sufficient cell yield can be obtained. Specifically, the culture is performed under such conditions that the volumetric oxygen transfer rate (KLa) becomes 250 $hr^{-1}$ or higher, for example, 300 hr' or higher, preferably 350 $hr^{-1}$ or higher, more preferably 380 hr' or higher, still more preferably 400 $hr^{-1}$ or higher, further preferably 500 hr$^{-1}$ or higher, still further preferably 750 hr$^{-1}$ or higher. The KLa value can be calculated by those skilled in the art as required. KLa can be adjusted by adjusting the aeration conditions and stirring conditions of culture liquid. The values of KLa used in the definition of the present invention, embodiments thereof, and examples thereof are those measured by the sulfurous acid oxidation method, unless especially indicated. The sulfurous acid oxidation method is a method advocated by Cooper (Ind. Eng. Chem., 36, 504-509, 1944).

Composition of the medium used for the culture of the yeast is not particularly limited, so long as the yeast can proliferate, and a sufficient cell yield can be obtained, and various kinds of media used in the production of yeast extracts can be used. As a carbon source, for example, any one selected from the group consisting of sugarcane blackstrap molasses, beet blackstrap molasses, cane sugar, wood chip cooking liquor, sulfite sulfite pulp waste liquid, sugarcane extract, glucose, acetic acid, and ethanol can be used. As a nitrogen source, for example, any one selected from the group consisting of nitrogen-containing organic substances such as yeast extract, peptone, corn steep liquor (CSL), and casein, urea, ammonia, and inorganic salts such as ammonium sulfate, ammonium chloride, and ammonium phosphate can be used. A phosphoric acid ingredient, potassium ingredient, and magnesium ingredient may be further added to the medium, and vitamins such as biotin, pantothenic acid, thiamine, inositol, and pyridoxine, and minerals such as zinc, copper, iron, and manganese may also be added. In order to supplement a growth promotion substance such as vitamin, extracts, peptone, and so forth may be added to the medium.

According to the investigations of the inventors of the present invention, it was found that if the amount of urea in the medium is decreased, succinic acid is more accumulated. That is, it was found that if the nitrogen source is reduced during the culture process to reduce the nitrogen content of the yeast, a larger amount of succinic acid is accumulated. It is estimated that decrease in nitrogen content of yeast cells inhibits advance of conversion of carbon compounds such as saccharides and aliphatic acids into nitrogen compounds such as amino acids, as a result, glutamic acid decreases, and succinic acid increases. Specifically, the nitrogen content of the yeast subjected to the organic acid generation treatment, i.e., the yeast obtained at the end of the culture, is made to have a nitrogen content of 8.5% or lower, preferably 8.0% or lower, more preferably 7.5% or lower, further preferably 7.0% or lower, based on dry weight of the yeast. Since unduly low nitrogen content of the yeast may provides insufficient accumulation of succinic acid, the nitrogen content of the yeast at the end of the culture is made to be 4.5% or higher, preferably 5.0% or higher, more preferably 5.5% or higher, further preferably 6.0% or higher, based on dry weight of the yeast.

The nitrogen amount based on dry yeast cell weight at the end of the culture can be adjusted by changing the amount of nitrogen contained in the medium used for the culture, specifically, by changing amount of an ingredient that serves as the nitrogen source such as urea. Other than urea, yeast extract, molasses, and so forth may serve as the nitrogen source. However, urea has a high nitrogen content per weight of the ingredient, and therefore in view of not significantly changing the composition of ingredients other than nitrogen, the amount of the nitrogen source in the medium is preferably adjusted by changing the amount of urea. The amount of urea in the medium may be, for example, 16 g/L or smaller, preferably 13 g/L or smaller, more preferably 11 g/L or smaller. As for the minimum amount, the nitrogen amount in the medium may be, for example, 5 g/L or larger, preferably 7 g/L or larger, more preferably 9 g/L or larger. The nitrogen amount based on dry weight of the yeast can be measured by the Kjeldahl method for a sample obtained by drying objective yeast (washed if needed). For performing the Kjeldahl method, an existing Kjeldahl analyzer (for example, Kjeltec System 2300, Foss Japan) can be used.

The culture conditions of the yeast can be appropriately designed by those skilled in the art depending on the yeast to be used. The conditions are not particularly limited so long as the yeast can proliferate, and sufficient cell yield can be obtained, and usual culture conditions used in the production of yeast extract can be applied. Specifically, the temperature may be 20 to 40° C., preferably 25 to 35° C., and pH may be 3.5 to 7.8, preferably 4.0 to 7.5. pH can be adjusted by an appropriate method. Culture time may be 30 hours or shorter, preferably 25 hours or shorter. Irrespective of the other conditions, the minimum culture time is not limited so long as the yeast can proliferate, and sufficient cell yield can be obtained, but it may be, for example, 5 hours or longer, preferably 7 hours or longer, more preferably 10 hours or longer.

Culture scheme can also be appropriately chosen by those skilled in the art depending on the yeast to be used and culture scale. It is not particularly limited so long as the yeast can proliferate, and sufficient cell yield can be obtained, and the culture may be performed as, for example, batch culture, fed-batch culture, or continuous culture. Culture tank is not also particularly limited so long as sufficient aerobic conditions can be provided, and conventional stirring culture tank, airlift culture tank, external circulation type culture tank, or culture tank comprising a combination of the mechanisms of the foregoings can be used.

For commercial culture of yest, yield based on saccharide (yield of yeast cells based on weight of saccharides used for the culture) is an extremely important factor, and how efficiently yeast cells are obtained from the sugar source used (sugarcane blackstrap molasses, beet blackstrap molasses, glucose, cane sugar, sugarcane juice solution, etc.) significantly affects the production cost. In order to maximize the yield based on saccharide, volume of air blown into the culture tank (aeration volume) is generally increased, and there are provided structures of the culture tank for the techniques of stirring the medium with a stirrer, externally circulating the culture liquid with a pump, efficiently dissolving oxygen contained in the air blown into the culture tank in the culture medium by providing a partition in the inside of the culture tank to circulate the culture liquid with air bubbles, and so forth, so that DO (dissolved oxygen) is maximized. These techniques can be used for the present invention.

In a particularly preferred embodiment, the culture is performed by using such a highly efficient culture tank with stirring at 600 rpm or faster and aeration volume of 0.8 vvm or larger (vvm=volume per volume per minute, gas supplying volume per unit volume) for increasing the yield based on saccharide. The culture is preferably performed with stirring at 650 to 800 rpm and aeration volume of 1.0 to 2.0 vvm.

After the culture supernatant is removed by using a centrifugation machine such as nozzle separator, the cultured yeast cells are washed with pure water a plurality of times as required, and used in the organic acid generation treatment step as a suspension of yeast cells (yeast cream).

[Organic Acid Generation Treatment Step]

In the organic acid generation treatment step, the organic acid content of the yeast is increased by maintaining the cultured yeast as the suspension under the conditions effective for organic acid generation. The organic acid is any one selected from the group consisting of succinic acid, lactic acid, and acetic acid, and from the viewpoint of the property of increasing umami, it is preferably lactic acid or succinic acid, more preferably succinic acid. When production of a larger amount of succinic acid is intended, this step is carried out under conditions effective for generation of succinic acid.

Specifically, the conditions effective for generation of organic acid (in a particularly preferred embodiment, conditions effective for generation of succinic acid) include gently stirring the suspension of the yeast. With this stirring, aeration may also be performed.

The conditions effective for generation of organic acid may also include maintaining the suspension of the yeast at 40 to 60° C., preferably 40 to 55° C., more preferably 45 to 50° C. Irrespective of the other conditions, pH is preferably 4.0 to 7.5, more preferably 6.0 to 7.0. pH can be controlled by an appropriate means.

For all the aforementioned conditions, the yeast suspension can be maintained under the conditions for 2 to 30 hours, or 2 to 24 hours, preferably 4 to 12 hours, further preferably 6 to 9 hours. Although a longer time of the organic acid generation treatment step is preferred from the viewpoint of stabilization of the accumulated amount of succinic acid or glutamic acid, it is preferably 9 hours or shorter from the viewpoint of preventing possible proliferation of bacteria in the environment, which causes decomposition.

The conditions effective for generation of organic acid mentioned above are particularly suitable for production of succinic acid. Therefore, the conditions mentioned above are also the conditions effective for generation of succinic acid.

While the inventors of the present invention investigated yeast extracts in which useful ingredients are enriched, they discovered a phenomenon that maintaining yeast under specific conditions induces generation of succinic acid. Succinic acid is synthesized from isoleucine in the glyoxylate cycle, or from glutamic acid via GABA in the GABA pathway, or converted from succinyl-CoA or fumaric acid in the TCA cycle. It is estimated that the maintenance under specific conditions promotes such enzymatic reactions as mentioned above in the yeast cells.

According to the investigation of the inventors of the present invention, autolysis treatment of yeast usually causes structural decomposition of yeast by autolysis, but the organic acid generation treatment does not cause autolysis, or causes autolysis only extremely partially, if it is caused, and the structures of the yeast cells can be maintained. It can be considered that, in the organic acid generation treatment step, the organic acid is produced by using the yeast cells as bioreactors. Therefore, it can be said that the organic acid generation treatment step is a step different form the conventional autolysis treatment step.

The objective organic acid is generated from a precursor accumulated in the yeast cells during the organic acid generation treatment step. In addition, the glutamic acid content of the yeast is also increased by the conditions effective for generation of organic acid. Since glutamic acid can also serve as a raw material for succinic acid production in the GABA pathway as described above, the conditions effective for generation of succinic acid may reduce the content of glutamic acid. However, according to the investigation of the inventors of the present invention, it was found that the conditions effective for generation of organic acid (they are also the conditions effective for generation of succinic acid) mentioned above increase not only production amount of an organic acid, but also production amount of glutamic acid.

The yeast suspension that has undergone the organic acid generation treatment step is then subjected to the hot water extraction step.

[Hot Water Extraction Step]

From the yeast suspension that has undergone the organic acid generation treatment step, yeast extract is extracted with hot water. The hot water extraction is performed by using hot water at, for example, 56° C. or higher, preferably 65 to 95° C., more preferably 75 to 85° C. For all the temperature, the extraction is performed for at least 10 minutes or longer, for example, 20 minutes or longer, preferably 30 minutes or longer.

Since the liquid obtained after the hot water extraction contains water-soluble extracted ingredients and insoluble ingredients such as yeast cell walls, an operation for separating or removing insoluble ingredients can be performed with a centrifugation machine such as nozzle separator. The water-soluble extracted ingredients are usually obtained as yeast extract.

The obtained yeast extract can be treated for clarification as required with a ceramic filter, fine membrane filter (MF), leaf filter, or oliver filter. The obtained yeast extract can be concentrated with a concentrator and thereby made into a pasty yeast extract, if needed.

The obtained yeast extract as it is, or the yeast extract to which an excipient such as maltodextrin, starch, or modified starch is added can be dried with a drier such as spray dryer, freeze dryer, or drum dryer, and thereby powdered to obtain yeast extract in the form of powder. The powder can also be granulated with a fluidized bed granulator as a subsequent step to obtain granular yeast extract that can be easily used.

[Yeast Extract]

The yeast extract obtained as described above contains 5.0% by weight or more, preferably 6.0% by weight or more, more preferably 10.0% by weight or more, of succinic acid based on the dry weight of the yeast extract, when a yeast belonging to the genus *Saccharomyces* is used as the yeast. According to a preferred embodiment, irrespective of the succinic acid content, the yeast extract contains 10.0% by weight or more, preferably 13.0% by weight or more, more preferably 15.0% by weight or more, of glutamic acid.

Alternatively, when a yeast belonging to the genus *Candida* is used as the yeast, the yeast extract contains 2.0% by weight or more, preferably 4.0% by weight or more, more preferably 5.0% by weight or more, of succinic acid based on the dry weight of the yeast extract. According to a preferred embodiment, irrespective of the succinic acid content, such a yeast extract contains 6.0% by weight or more, preferably 7.0% by weight or more, more preferably 9.0% by weight or more, of glutamic acid.

According to the investigation of the inventors of the present invention, with the yeast extract obtained according to the present invention, which contains succinic acid and glutamic acid at high concentrations, any one selected from the group consisting of initial taste (saki-aji), richness (koku-mi, koku-aji), and taste of foods can be improved. Seafood flavor or taste of foods of which raw material contains seafood can also be improved.

Whether any one selected from the group consisting of initial taste, richness, and taste is improved or not, and degree of the improvement can be evaluated as required by those skilled in the art using organoleptic evaluation methods for foods. For the evaluation, organoleptic evaluation criteria can be established. As for more specific evaluation methods and criteria, the examples of the present invention mentioned later can be referred to.

According to the investigation of the inventors of the present invention, it was considered that, in the yeast extract containing succinic acid and glutamic acid at high contents, besides the synergistic effect of taste nucleic acid and glutamic acid, synergistic effect is also provided by succinic acid, and so forth (refer to Examples 12 and 13). That is, the yeast extract having high contents of succinic acid and glutamic acid provided by the present invention, specifically, the yeast extract containing 5.0% by weight or more, preferably 6.0% by weight or more, more preferably 10.0% by weight or more, of succinic acid, and 10.0% by weight or more, preferably 13.0% by weight or more, more preferably 15.0% by weight or more, of glutamic acid based on the dry weight of the yeast extract, obtained by using a yeast belonging to the genus *Saccharomyces*, or the yeast extract containing 2.0% by weight or more, preferably 4.0% by weight or more, more preferably 5.0% by weight or more, of succinic acid, and 6.0% by weight or more, preferably 7.0% by weight or more, more preferably 9.0% by weight or more, of glutamic acid based on the dry weight of the yeast extract, obtained by using a yeast belonging to the genus *Candida* provides novel synergistic effect exerted by succinic acid, and so forth.

The yeast extract provided by the present invention, which is produced by the production method of the present invention, originates in culture (fermentation product) of yeast, and contains many kinds of ingredients. Moreover, it is considered that, during the organic acid generation treatment step, useful ingredients are produced by enzymes relating to metabolic systems remaining in yeast cells under specific conditions different from those of the culture, and the objective effect of improving any one selected from the group consisting of initial taste, richness, and taste is attained by the actions of the various ingredients produced as described above. Therefore, in order to identify ingredients that contribute to the objective effect by analyzing the composition of the yeast extract of the present invention, which is obtained from culture as a raw material and has undergone the organic acid generation treatment step and the hot water extraction step, such identification should be performed for a huge number of kinds of complicated ingredients contained in the yeast extract. Further, if the objective effect is attained by interactions of a plurality of kinds of ingredients, there should be required a huge number of experiments for confirming effect for every combination of identified trace amount ingredients. In addition, for such experiments, in order to completely eliminate influences of other substances, all of a large number of candidate trace amount ingredients must be purified to high purity. Then, it is considered that it is utterly unpractical to directly specify the yeast extract of the present invention with the composition or characteristics thereof.

When the yeast extract of the present invention is added to foods, the minimum addition amount thereof is not particularly limited so long as the objective effect is obtained. Irrespective of type of food, the addition amount may be 0.001% or larger, preferably 0.002% or larger, more preferably 0.004% or larger, further preferably 0.008% or larger, in terms of amount of dry yeast extract.

The maximum addition amount can be determined so that balance of original tastes and flavors of objective food is not degraded by tastes and flavors of the yeast extract. From such a point of view, for any type of food, the addition amount may be, for example, 5% or smaller, preferably 4% or smaller, more preferably 3% or smaller, further preferably 2% or smaller. So that the tastes and flavors originating in the yeast extract are not sensed, the addition amount is preferably 1% or smaller, more preferably 0.5% or smaller.

For foods of which raw material includes seafood, the addition amount may be 0.001% or larger, preferably 0.002% or larger, more preferably 0.004% or larger, further preferably 0.008% or larger, and 0.5% or smaller, preferably 0.4% or smaller, more preferably 0.3% or smaller, further preferably 0.2% or smaller, in terms of amount of dry yeast extract. So that the tastes and flavors originating in the yeast extract are not sensed, the addition amount is preferably 0.1% or smaller, more preferably 0.05% or smaller.

[Seasoning Composition and Others]

The present invention provides a seasoning composition containing a yeast extract that contains 5.0% by weight or more of succinic acid and 10.0% by weight or more of glutamic acid based on dry weight of the yeast extract. Such a seasoning composition is especially suitable for improving any one selected from the group consisting of initial taste, richness, and taste of foods, or for improving seafood flavor or taste of foods of which raw material contains seafood.

The seasoning composition may consist of the yeast extract alone, or a mixture of the yeast extract with other seasonings, for example, soy sauce, miso (soy bean paste), oyster sauce, salt, sugar, protein hydrolysate, and other food materials.

The seasoning composition may contain an ingredient other than the yeast extract, so long as the yeast extract can exhibit the objective effect. The other ingredient may be any of various additives allowed for foods. Examples include antioxidant (anti-oxidation agent), perfume, sweetener, coloring agent, thickening stabilizer, color developer, bleaching agent, antifungal agent, gum base, bitterant, seasoning, enzyme, brightener, acidulant, emulsifier, binder, isotonic agent, buffering agent, dissolving aid, preservative, stabilizer, coagulant, and so forth.

The present invention provides a food obtained by using the yeast extract or the seasoning composition containing the yeast extract. Foods to which the yeast extract or the seasoning composition is preferably added are, for example, foods of which raw material contains seafood.

Specific examples of the foods include soups and soup bases (for example, fumet de poisson (fish stock used for European foods), bouillabaisse, consomme, corn soup, onion soup, tomato soup, miso soup, Japanese clear soup, ramen noodle soup, Japanese noodle soup), seasoning compositions (for example, chicken consomme, beef consomme, chemical seasoning composition, seasoning salt composition, mayonnaise, tomato ketchup, Worcestershire sauce, sauce for pork cutlet, sauce other than Western style sauce, dressing, herb salt, miso, soy sauce, noodle dipping sauce, soup stock), sauces (for example, white sauce, demiglace sauce, tomato sauce, meat sauce, curry roux, pasta sauce), ground fish meat products (for example, chikuwa (fishcake tube), sasa-kamaboko (bamboo grass leaf-shaped steamed fish paste), datemaki (tightly rolled sweet fish omelette), kamaboko (steamed fish paste), fish sausage, hanpen (puffy cake of steamed ground fish combined with starch), tsumire (dumpling made of ground fish), narutomaki (fish paste loaf with whirlpool pattern), Satsuma-age (deep-fried ground fish paste), ebiten (deep-fried ground fish and prawn), jakoten (deep-fried ground small fish)), meat products (for example, hams such as boneless ham, pork loin ham, raw ham, bone-in ham, and pressed ham; sausages such as Vienna sausage, dry sausage, Frankfurt sausage, Boronia sausage, and Lyonnaise sausage; bacons; corned beef; roast pork), cheese, butter, snack confectioneries (for example, potato chips, popcorn, cone snack, cracker, biscuit, cookie, pretzel), retort pouch daily dish, chilled daily dish, frozen daily dish, instant noodles, and fries (for example, fried potato, fried chicken, fried fish). Examples also include breads, nan, edible wrapping sheet (for example, pizza crust, pie crust, wrapping sheet for gyoza (Chinese meat dumpling), wrapping sheet for shumai (steamed meat dumpling)), tortilla, taco shell, cornflakes, and noodles (for example, pasta, Japanese noodles, rice vermicelli, as raw, dried, and fried noodles) and premixes therefor, and preservable foods (for example, pickles in vinegar, pickles in salt).

Such foods as described above can be produced by using known techniques. The present invention also provides a method for producing a food, which comprises the step of adding a yeast extract containing 5.0% by weight or more of succinic acid and 10.0% by weight or more of glutamic acid based on dry weight of the yeast extract to a food to obtain a food of which any one selected from the group consisting of initial taste, richness, and taste is improved, and a method for producing a food, which comprises the step of adding a yeast extract containing 5.0% by weight or more of succinic acid and 10.0% by weight or more of glutamic acid based on dry weight of the yeast extract to a food of which raw material contains seafood to obtain a food of which seafood flavor or taste is improved. The step of adding the yeast extract or the seasoning composition may be performed at any of various stages of food manufacturing processes. Those skilled in the art can appropriately design production steps of foods containing the ingredients at predetermined ratios and/or concentrations at the time of eating, in consideration of solubility, stability, volatility, and so forth of the ingredients.

Hereafter, the present invention will be explained in still more detail with reference to examples. However, the present invention is not limited by the following examples.

EXAMPLES

In the following examples, investigations were performed with the following materials and methods, unless especially indicated.

<Used Strains>

The *Saccharomyces cerevisiae* SC21 strain mainly used in the examples of the present invention was obtained as follows.

This strain was obtained by performing citric acid resistance screening for cells of the FT4 strain (accession number FERM BP-8081). The FT4 strain cells were cultured in the YPD medium (1.0% of Bacto yeast extract (DIFCO), 2.0% of Bacto peptone (DIFCO), 2.0% of glucose) until they reached the logarithmic phase, then collected and washed. The cells were suspended in a 0.067 M potassium phosphate solution, and irradiated with ultraviolet rays for 2 minutes with stirring. Then, the cells were cultured on the SD agar medium (0.67% of Yeast Nitrogen Base w/o Amino Acid (DIFCO), 2.0% of glucose, 2.0% of agar) containing 75 mM citric acid at 30° C. for 5 days, and 30 strains that showed high proliferation rate were obtained as citric acid resistant strains. Cells of these 30 yeast strains were each cultured in 50 ml of the YPD medium for 24 hours, and then collected by centrifugation, and lyophilized cells thereof were prepared. Intracellular ingredients were extracted from the prepared lyophilized cells at 95° C. for 20 minutes, the extraction liquid was centrifuged, and organic acids and amino acids in the supernatant were measured by HPLC. As a result, the SC21 strain having high succinic acid and glutamic acid contents was obtained.

<Methods for Measuring Organic Acid and Amino Acid>

Methods for Measuring Organic Acid:

The supernatant obtained by centrifugation after the hot water extraction was filtered through a 0.45-μm filter to prepare a sample for measurement, and organic acid content thereof was measured by HPLC. The HPLC conditions were as follows.

Column: GL-C610 H-S(Hitachi High-Tech)

Column temperature: 56° C.

Eluent: 3 mM Perchloric acid; flow rate, 0.5 ml/minute

Reaction mixture: 0.21% Disodium hydrogenphosphate and 0.00938% bromothymol blue; flow rate, 0.5 ml/minute Detection: UV 430 nm The measured values are indicated in terms of concentration (%) based on dry weight of the sample.

Method for Measuring Amino Acid

The supernatant obtained by centrifugation after the hot water extraction was filtered through a 0.20-μm filter to prepare a measurement sample, and amino acid contents thereof were measured by using an amino acid analyzer (Hitachi L-8900). Ninhydrine was used for the reaction mixture. The measured values are indicated in terms of concentration (%) based on dry weight of the sample.

<Method for Measuring Dry Weight of Sample>

The dry weight was obtained by weighing 5 g of a sample on an aluminum dish of which tare weight was measured beforehand, drying the sample at 105° C. for 6 hours in a drier, and measuring the weight after drying.

Experimental Methods

<Preculture>

The yeast cells used for the main culture were prepared as follows.

(1) The YPD medium (200 ml) was put into each of five 500-ml baffled flasks.

(2) The YPD medium was autoclaved (121° C., 15 minutes).

(3) The *Saccharomyces cerevisiae* SC21 strain was inoculated into the autoclaved YPD medium, and cultured under the following conditions.

Culture temperature: 30° C.

Shaking: 200 rpm (rotary shaker)

Culture time: 24 hours

After completion of the preculture, the collected yeast cells were washed, and water was added to the cells to prepare a yeast suspension containing 100 g/L of yeast in terms of dry yeast weight.

<Main Culture>

The main culture was performed with a volume of 1.2 L at the time of the start of the culture, so that the volume became 1.7 L at the end of feeding. That is, 1.15 L of a medium having the following composition was first sterilely prepared directly in a 3-L jar fermenter (ABLE). Then, the main culture was performed with feeding sugarcane blackstrap molasses adjusted to have a sugar content of 43% (henceforth referred to as "molasses") in such an appropriate volume that growth inhibition is not caused by generated alcohol, so that the volume finally became 1.7 L. The culture time was 15 hours.

(Composition of Starting Medium)

| | |
|---|---|
| Urea | 20 g |
| Phosphoric acid | 1.5 ml |
| Magnesium sulfate heptahydrate | 0.3 g |
| Yeast extract | 1.2 g |

Distilled water was added to obtain a total volume of 1.15 L.
(Culture conditions)
Inoculation amount: 50 ml of yeast suspension
Culture temperature: 32° C.
Aeration: 1.7 L/minute
Stirring: 650 rpm
Kla: 500 hr' at the end of the culture
pH Control: 4.5 as the lowest pH (adjusted by addition of 15% sodium carbonate) Feed medium: Molasses (sugar content, 43%); volume, 500 ml (added portionwise in appropriate volumes so that growth inhibition was not caused)
<Conditions for Organic Acid Generation Treatment>
The yeast cells collected from the culture liquid were washed, then water was added to the cells to obtain a yeast suspension containing 170 g/L of the yeast in terms of dry yeast weight, and the suspension was subjected to the organic acid generation treatment under the following conditions.
Temperature: 45° C.
pH: Uncontrolled (pH 5.0 to 6.5)
Time: 6 Hours (with stirring in such a speed that the yeast suspension did not foam)
The dry yeast weight was obtained by weighing 5 g of the yeast suspension on an aluminum dish of which tare weight was measured beforehand, drying the suspension at 105° C. for 6 hours in a drier, and measuring the weight after drying.
<Conditions for Hot Water Extraction>
The yeast suspension was subjected to hot water extraction under the following conditions, and then the insoluble ingredients were separated by using a centrifugal machine.
Temperature: 85° C.
Time: 30 Minutes
Stirring: Stirring at Such a Speed that the Yeast Suspension Did not Get Burned on the internal surface of the container.
<Filtration Conditions>
The yeast extract obtained after the insoluble ingredients were removed was filtered through a precision filtration membrane.
Filtration membrane: Microza UMP-153 (Asahi Kasei Chemicals)
<Concentration conditions>
The filtered yeast extract was concentrated in a rotating evaporator (NE, EYELA).
(Conditions)
Water bath temperature: 60° C.
Revolving speed of flask: 100 rpm
Solid content at the end of concentration: 45.9%
<Method for Calculating KLa Value>
KLa was calculated in accordance with the following equation on the basis of the sulfurous acid oxidation method.

$$OTR = KLa(C^* - C)$$

OTR is oxygen transfer rate (mmol/l·hr), $C^*$ is saturated dissolved oxygen concentration (mmol/l), and C is dissolved oxygen concentration (mmol/l).
OTR was calculated on the basis of the oxidation reaction of sodium sulfite shown below.

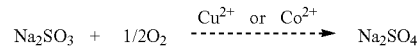

That is, sodium sulfite is oxidized into sodium sulfate by a zero-order reaction in the presence of copper or cobalt. Therefore, the oxidation rate of sodium sulfite is equal to the oxygen transfer rate. In such a case, dissolved oxygen concentration C is 0 (mmol/l).
Experimental Procedure
An aqueous solution containing 1 mM copper sulfate and at least 15 mM sodium sulfite is aerated under fixed conditions. With a fixed interval, the solution is sampled, and unoxidized sulfurous acid in the sample is oxidized with an excess amount of iodine. Then, the concentration of sulfurous acid in the sample is measured by back titration of the excessive iodine with sodium thiosulfate. By using temporally changing concentrations of sulfurous acid in the following equation, KLa is calculated.

$$KLa = (C1-C2)/2C^*(t2-t1)$$

C1 and C2 (mmol/l) are sulfurous acid concentrations observed after arbitrary times t1 and t2 from the start of the aeration, respectively. $C^*$ is the saturated oxygen concentration (mmol/l).
KLa was actually calculated as follows.
Specifically, in this experiment, 1.6 L of 50 to 150 mM sodium sulfite aqueous solution was added to a 3-L volume culture tank (ABLE), and amount of sulfurous acid was measured over time with aeration by stirring. Aeration volume was fixed to be 1.7 L, and the stirring speed was set to be 100, 300, 450, 600, or 750 rpm. The concentration of the sodium sulfite aqueous solution was increased according to increase of the stirring speed.
<Measurement of Total Nitrogen Amount of Lyophilized Cells>
(Preparation of Lyophilized Cells)
(1) Yeast cells are separated from 20 ml of the culture liquid by centrifugation, and washed twice with distilled water.
(2) The washed yeast cells are frozen at −80° C. for 2 hours.
(3) The frozen cells are dried in a vacuum dryer (FRD-50P, IWAKI) for 24 hours.
(Preparation of measurement sample)
(1) A sample (0.5 g) is taken, and put into a container that can be heated.
(2) One pellet of Kjeltab Cu/4.5 is put into the container.
(3) Concentrated sulfuric acid (10 ml) is added.
(4) Hydrogen peroxide (7 ml) is gradually added.
(5) The decomposition reaction is allowed at 420° C. for 3 hours.
(6) The reaction mixture is left until it is cooled.
(Measurement of Total Nitrogen)
Used apparatus: Kjeltec 2300
Conversion equation: 0.14007×Volume of 1% boric acid solution required for titration (ml)/Sample weight Example 1: Investigation of Aeration Volume The *Saccharomyces cerevisiae* SC21 strain was cultured under the conditions of stirring speed of 100, 300, 450, 600, or 750 rpm, and aeration of 1.6 L/min. The organic acid generation treatment was performed for the yeast cells obtained with the each stirring speed conditions, and it was verified whether succinic acid would increase in the yeast suspension after the organic acid generation treatment. Since stirring at 750 rpm or faster is considered to be impossible in actual production, and therefore stirring at such a speed is not studied.

<Preculture>

Yeast cells used for the main culture were prepared as follows.

(1) The following medium (100 g) was put into each of fourteen 500-ml baffled flasks.
(2) The medium was autoclaved (121° C., 15 minutes).
(3) The *Saccharomyces cerevisiae* SC21 strain was inoculated into the autoclaved medium, and cultured under the following conditions.

(Medium Composition)

| | |
|---|---|
| Molasses | 18.6 g |
| Urea | 0.6 g |
| $(NH_4)_2SO_4$ | 0.16 g |
| $(NH_4)_2HPO_4$ | 0.08 g |

Distilled water was added to obtain a total weight of 100 g.

(Culture Conditions)
Culture temperature: 30° C.
Shaking: 160 rpm (rotary shaker)
Culture time: 24 hours <Main Culture>

The main culture was performed with a volume of 1.2 L at the start of the culture, so that the volume became 1.6 L at the end of feeding. A 3-L jar fermenter (ABLE) was used.

(Composition of Starting Medium)

| | |
|---|---|
| $NH_4Cl$ | 5.3 g |
| $(NH_4)_2HPO_4$ | 1.2 g |

A total volume of 1.02 L was obtained by adding distilled water.

(Culture Conditions)
Inoculation amount: 180 ml of preculture liquid
Culture temperature: 30° C.
Aeration: 1.6 L/minute
Stirring: 100, 300, 450, 600, 750 rpm
pH Control: 4.5 as the lowest pH (adjusted by addition of 15% sodium carbonate)
Feed medium: Molasses (sugar content, 43%); volume, 400 ml (added portion wise in appropriate volumes so that growth inhibition was not caused)
Culture time: 24 hours <Conditions for Organic Acid Generation Treatment>

The organic acid generation treatment was performed under the following conditions.
Temperature: 40, 48 or 55° C.
pH: Uncontrolled (pH 5.0 to 5.8)
Time: 38 Hours
Stirring: Stirring in such an intensity that the yeast suspension did not foam The results are shown in the following tables.

[Table 1]

TABLE 1

Culture conditions and results

| | Conditions 1 | Conditions 2 | Conditions 3 | Conditions 4 | Conditions 5 |
|---|---|---|---|---|---|
| Stirring speed (rpm) | 100 | 300 | 450 | 600 | 750 |
| Aeration volume (L/minute) | 1.6 | 1.6 | 1.6 | 1.6 | 1.6 |
| Culture volume/aeration volume (vvm) | 1 | 1 | 1 | 1 | 1 |
| KLa (hr−1) | 0.9 | 35 | 120 | 400 | 700 |
| Yield of dry cells (g) | 10.5 | 14.3 | 19.9 | 27.4 | 38.4 |
| Dry cell concentration in culture liquid (%) | 0.8 | 1 | 1.4 | 1.9 | 2.7 |

(Succinic acid %/Dry cell weight)

| | | Conditions 1 | Conditions 2 | Conditions 3 | Conditions 4 | Conditions 5 |
|---|---|---|---|---|---|---|
| Change of Succinic acid amount provided by organic acid generation treatment | | | | | | |
| Organic acid generation treatment temperature: 40° C. | | | | | | |
| Before organic acid generation treatment | | 0.52 | 0.54 | 0.57 | 0.89 | 0.84 |
| Organic acid generation treatment | 1.5H | 0.64 | 0.67 | 0.77 | 1.31 | 1.43 |
| | 14H | 0.87 | 1.01 | 1.35 | 2.00 | 2.43 |
| | 22H | 0.84 | 1.08 | 1.51 | 2.18 | 2.78 |
| | 38H | 0.93 | 1.21 | 1.57 | 2.76 | 3.19 |
| Organic acid generation treatment temperature: 48° C. | | | | | | |
| Before organic acid generation treatment | | 0.52 | 0.54 | 0.57 | 0.89 | 0.84 |
| Organic acid generation treatment | 14H | 0.82 | 0.93 | 1.19 | 1.89 | 2.10 |
| | 22H | 0.78 | 0.88 | 1.26 | 1.92 | 2.59 |
| Organic acid generation treatment temperature: 55° C. | | | | | | |
| Before organic acid generation treatment | | 0.52 | 0.54 | 0.57 | 0.89 | 0.89 |
| Organic acid generation treatment | 14H | 0.64 | 0.68 | 0.91 | 1.53 | 1.61 |
| | 22H | 0.64 | 0.66 | 0.86 | 1.42 | 1.67 |

(1) Results of Culture

When the culture was performed under the same culture conditions with changing only the stirring speed, a higher stirring speed provided higher cell yield. It is considered that this was because more efficient supply of oxygen provides more efficient proliferation of yeast.

(2) Succinic Acid Production Based on Dry Cells after Organic Acid Generation Treatment After the organic acid generation treatment, the highest concentration of succinic acid based on dry weight of the yeast was obtained with the yeast cultured under the high stirring speed conditions. This phenomenon was observed for all the organic acid generation treatment temperatures of 40° C., 48° C., and 55° C. However, under the conditions of 55° C., the yeast cells collapsed.

These results indicate that a higher stirring speed, i.e., a higher oxygen transfer volume, provides higher cell yield, as well as larger amount of succinic acid after the organic acid generation treatment.

Example 2: Confirmation of Influence of Organic Acid Generation Treatment on Other Organic Acids The *Saccharomyces cerevisiae* SC21 strain was cultured as the yeast, and a yeast cell suspension prepared by using the obtained yeast cells was subjected to the organic acid generation treatment. Through this investigation, it was verified how difference of the culture conditions affect change of the ingredient composition caused by the organic acid generation treatment.

The experimental conditions are shown in the following table.

TABLE 2-1

| Step | Detailed conditions |
| --- | --- |
| Preculture | Medium: YPD liquid medium<br>Temperature: 30° C.<br>Revolving speed of rotary shaker: 200 rpm<br>Culture time: 24 hours |
| ↓ | |
| Main culture | Medium: 20 g of urea, 1.5 ml of phosphoric acid, 0.3 g of magnesium sulfate heptahydrate, 1.2 g of yeast extract; total volume of 1.15 L was obtained with distilled water<br>Inoculation amount: 50 ml of yeast suspension (dry yeast weight, 5 g)<br>Temperature: 32° C.<br>Aeration: 1.7 L/minute<br>Stirring speed: 650 rpm<br>KLa at the end of the culture: 500 hr$^{-1}$<br>pH Control: 4.5 as the lowest pH (adjusted by addition of 15% sodium carbonate)<br>Feed medium: Molasses (sugar content, 43%); volume, 500 ml<br>Culture period: 15 hours |
| ↓ | |
| Collection and washing of cells | Centrifugal separation (→ obtain cells for organic acid generation treatment) |
| ↓ | |
| Organic acid generation treatment | Temperature: 45° C.<br>Time: 6 hours<br>pH control: Uncontrolled<br>Stirring: Stirred (with stirrer bar)<br>Dry yeast weight (solid content): 15% |

The results are shown in the following table.

TABLE 2-2

| | Before organic acid generation treatment | (%/Dry yeast weight) After organic acid generation treatment |
| --- | --- | --- |
| Citric acid | 0.56 | 0.30 |
| Malic acid | 0.14 | 0.03 |
| Succinic acid | 0.31 | 0.98 |
| Lactic acid | 0.06 | 0.30 |
| Acetic acid | 0.02 | 0.25 |
| Pyroglutamic acid | 0.52 | 0.52 |

In the yeast suspension, succinic acid amount markedly increased after the organic acid generation treatment compared with that observed before the organic acid generation treatment, and acetic acid and lactic acid amounts slightly increased, based on the dry weight of the yeast. On the other hand, citric acid amount decreased. On the basis of the above results, it was found that the organic acid contents, especially the succinic acid content, in the yeast suspension change during the process of the organic acid generation treatment for 6 hours.

Example 3: Investigation of Amino Acid Contents

Then, changes of amino acid contents were examined. Amounts of ingredients contained in yeast suspensions and yeast extracts obtained after the organic acid generation treatment were also examined.

The experimental conditions for the preculture to the organic acid generation treatment were the same as those of Example 1. After heat sterilization treatment, insoluble ingredients were removed by centrifugation to obtain a yeast extract (water-soluble ingredients).

The results are shown in the following table.

TABLE 3

| Yeast suspension | | | Yeast extract | |
|---|---|---|---|---|
| Organic acid generation | (%/Dry yeast weight) | | | |
| treatment time | 0 | 6 | | (%/Dry yeast extract weight) |
| Citric acid | 0.57 | 0.32 | Citric acid | 1.61 |
| Malic acid | 0.19 | 0.02 | Malic acid | 0.05 |
| Succinic acid | 0.57 | 1.34 | Succinic acid | 4.52 |
| Lactic acid | 0.16 | 0.24 | Lactic acid | 0.83 |
| Acetic acid | 0.02 | 0.26 | Acetic acid | 0.93 |
| Pyroglutamic acid | 0.45 | 0.43 | Pyroglutamic acid | 0.80 |
| Asp | 0.19 | 0.04 | Asp | 0.15 |
| Thr | 0.67 | 0.61 | Thr | 2.58 |
| Ser | 0.07 | 0.08 | Ser | 0.26 |
| Glu | 5.66 | 5.91 | Glu | 23.80 |
| Gly | 0.12 | 0.18 | Gly | 0.62 |
| Ala | 1.14 | 1.3 | Ala | 4.50 |
| Cys | 0.22 | 0.24 | Cys | 0.79 |
| Val | 0.14 | 0.21 | Val | 0.71 |
| Met | 0.04 | 0.08 | Met | 0.28 |
| Ile | 0.21 | 0.29 | Ile | 0.96 |
| Leu | 0.09 | 0.14 | Leu | 0.37 |
| Tyr | 0.04 | 0.05 | Tyr | 0.07 |
| Phe | 0.06 | 0.06 | Phe | 0.14 |
| Lys | 0.05 | 0.09 | Lys | 0.29 |
| His | 0.04 | 0.05 | His | 0.18 |
| Arg | 0.33 | 0.38 | Arg | 1.29 |
| Pro | 0.14 | 0.32 | Pro | 0.93 |
| Total | 9.21 | 9.46 | Total | 37.90 |

As for organic acids, succinic acid and acetic acid increased, and citric acid decreased. The results were basically the same as those of Example 2. As for amino acids, glutamic acid, alanine, and proline slightly increased, and aspartic acid decreased. On the basis of these results, it was found that the organic acid generation treatment increases or decreases not only organic acids, but also amino acids.

Example 4: Influence of Prolongation of Treatment Time

Since it was estimated that the organic acid generation reactions are enzymatic reactions, in order to examine whether extended organic acid generation treatment time provides the same result, an experiment was performed in the same manner as that of Example 1 except that the organic acid generation treatment time was extended to 12 hours, and change of the ingredients in the yeast suspension was examined.

The results are shown in the following table.

TABLE 4

| | (%/Dry yeast weight) | |
|---|---|---|
| Organic acid generation treatment time | 0 | 12 |
| Citric acid | 0.75 | 0.18 |
| Malic acid | 0.14 | 0.05 |
| Succinic acid | 0.70 | 2.65 |
| Lactic acid | 0.10 | 0.26 |
| Acetic acid | 0.05 | 0.91 |
| Pyroglutamic acid | 0.36 | 0.26 |

As observed in Example 1, after the organic acid generation treatment, succinic acid and acetic acid markedly increased, lactic acid slightly increased, and citric acid decreased. It also became clear that magnitudes of the changes are increased by prolongation of the organic acid generation treatment time.

In consideration of the results of the above investigations, the following investigations were performed with paying attention to change of amount of glutamic acid, which is an important taste ingredient for production of seasonings, in addition to succinic acid that is increased by the organic acid generation treatment.

Example 5: Influence of pH

In order to examine influence of pH at the time of the organic acid generation treatment, experiments were performed with controlling pH at the time of the organic acid generation treatment to be 3 to 7.

The results are shown in the following table.

TABLE 5

| | | | | | (%/Dry yeast weight) Variation between |
|---|---|---|---|---|---|
| Organic acid generation treatment time | 0 | 2 | 12 | 15 | 0 to 15 |
| pH 7.0 (fixed) | | | | | |
| Citric acid | 0.66 | 0.45 | 0.14 | 0.05 | −0.60 |
| Malic acid | 0.09 | 0.01 | 0.05 | 0.03 | −0.06 |
| Succinic acid | 0.75 | 1.00 | 2.20 | 2.32 | 1.57 |
| Lactic acid | 0.12 | 0.13 | 0.36 | 0.39 | 0.27 |
| Acetic acid | 0.05 | 0.24 | 0.86 | 1.08 | 1.03 |
| Pyroglutamic acid | 0.46 | 0.48 | 0.38 | 0.33 | −0.13 |
| pH 6.0 (fixed) | | | | | |
| Citric acid | 0.66 | 0.71 | 0.20 | 0.15 | −0.51 |
| Malic acid | 0.09 | 0.06 | 0.02 | 0.03 | −0.06 |
| Succinic acid | 0.74 | 1.22 | 1.92 | 1.97 | 1.22 |
| Lactic acid | 0.11 | 0.33 | 0.22 | 0.22 | 0.11 |
| Acetic acid | 0.04 | 0.22 | 0.63 | 0.67 | 0.63 |
| Pyroglutamic acid | 0.49 | 0.41 | 0.66 | 0.54 | 0.05 |
| pH 5.0 (fixed) | | | | | |
| Citric acid | 0.66 | 0.42 | 0.24 | 0.20 | −0.46 |
| Malic acid | 0.09 | 0.07 | 0.02 | 0.03 | −0.06 |
| Succinic acid | 0.74 | 1.19 | 1.52 | 1.55 | 0.81 |
| Lactic acid | 0.11 | 0.39 | 0.08 | 0.04 | −0.07 |
| Acetic acid | 0.04 | 0.18 | 0.55 | 0.56 | 0.52 |
| Pyroglutamic acid | 0.49 | 0.38 | 0.70 | 0.60 | 0.11 |
| pH 4.0 (fixed) | | | | | |
| Citric acid | 0.66 | 0.63 | 0.32 | 0.34 | −0.32 |
| Malic acid | 0.09 | 0.04 | 0.00 | 0.01 | −0.08 |
| Succinic acid | 0.74 | 1.21 | 1.05 | 1.09 | 0.35 |
| Lactic acid | 0.11 | 0.23 | 0.07 | 0.07 | −0.04 |
| Acetic acid | 0.04 | 0.19 | 0.35 | 0.35 | 0.31 |
| Pyroglutamic acid | 0.49 | 0.50 | 0.79 | 0.73 | 0.24 |
| pH 3.0 (fixed) | | | | | |
| Citric acid | 0.66 | 0.58 | 0.39 | 0.39 | −0.28 |
| Malic acid | 0.09 | 0.03 | 0.02 | 0.01 | −0.08 |
| Succinic acid | 0.74 | 1.10 | 1.01 | 1.01 | 0.27 |
| Lactic acid | 0.11 | 0.18 | 0.04 | 0.05 | −0.06 |
| Acetic acid | 0.04 | 0.19 | 0.32 | 0.32 | 0.28 |
| Pyroglutamic acid | 0.49 | 0.48 | 0.87 | 0.86 | 0.37 |

It was revealed that succinic acid content changes pH-dependent manner, and as pH value shifts to the alkalinity side, variation of the content becomes larger. As far as investigated so far, it was revealed that increase amount of acetic acid, decrease amount of citric acid, and so forth are also larger on the alkalinity side, and the highest succinic acid content was observed at pH 7, which was the nearest to the alkalinity side.

Example 6: Influence of pH Change on Amino Acid Amounts

Then, amino acids were further analyzed with changing pH at the time of the organic acid generation treatment within the range of 5.8 to 7.5. The experimental conditions were the same as those of Example 4.

The results are shown in the following table.

TABLE 6

| | | | | | | | | | (%/Dry yeast weight) |
|---|---|---|---|---|---|---|---|---|---|
| | | | | | pH | | | | |
| | 5.8 | | 6.2 | | 6.8 | | 7.5 | | |
| | Organic acid generation treatment time | | | | | | | | |
| | 0 | 6 | 9 | 6 | 9 | 6 | 9 | 6 | 9 |
| Citric acid | 0.35 | 0.23 | 0.13 | 0.16 | 0.09 | 0.14 | 0.09 | 0.12 | 0.09 |
| Malic acid | 0.11 | 0.03 | 0.02 | 0.02 | 0.03 | 0.03 | 0.02 | 0.03 | 0.03 |
| Succinic acid | 0.60 | 1.35 | 1.41 | 1.59 | 1.67 | 1.91 | 1.95 | 1.35 | 1.39 |
| Lactic acid | 0.06 | 0.24 | 0.14 | 0.35 | 0.24 | 0.79 | 0.79 | 0.50 | 0.48 |
| Acetic acid | 0.19 | 0.84 | 0.90 | 0.94 | 1.05 | 0.83 | 0.89 | 0.74 | 0.92 |
| Pyroglutamic acid | 0.36 | 0.46 | 0.52 | 0.27 | 0.28 | 0.16 | 0.16 | 0.21 | 0.29 |
| Asp | 0.08 | 0.04 | 0.05 | 0.05 | 0.06 | 0.21 | 0.15 | 0.06 | 0.08 |
| Thr | 0.49 | 0.67 | 0.54 | 0.25 | 0.28 | 0.14 | 0.11 | 0.19 | 0.14 |
| Ser | 0.09 | 0.11 | 0.11 | 0.08 | 0.08 | 0.04 | 0.03 | 0.04 | 0.04 |
| Glu | 4.09 | 3.55 | 3.66 | 4.27 | 4.74 | 5.45 | 5.45 | 5.11 | 5.21 |
| Gly | 0.03 | 0.07 | 0.09 | 0.09 | 0.13 | 0.26 | 0.3 | 0.26 | 0.27 |
| Ala | 2.01 | 2.29 | 2.32 | 2.26 | 2.46 | 2.73 | 2.73 | 2.31 | 2.51 |
| Cys | 0.13 | 0.13 | 0.13 | 0.12 | 0.14 | 0.18 | 0.19 | 0.22 | 0.23 |
| Val | 0.15 | 0.23 | 0.23 | 0.27 | 0.3 | 0.48 | 0.47 | 0.37 | 0.39 |
| Met | 0 | 0.02 | 0.03 | 0.02 | 0.02 | 0 | 0 | 0.00 | 0.00 |
| Ile | 0.07 | 0.1 | 0.11 | 0.09 | 0.1 | 0.11 | 0.11 | 0.10 | 0.10 |
| Leu | 0.04 | 0.07 | 0.09 | 0.06 | 0.08 | 0.07 | 0.07 | 0.06 | 0.06 |
| Tyr | 0.03 | 0.04 | 0.04 | 0.04 | 0.04 | 0.04 | 0.05 | 0.04 | 0.04 |
| Phe | 0.06 | 0.07 | 0.07 | 0.06 | 0.07 | 0.06 | 0.07 | 0.07 | 0.08 |
| Lys | 0.01 | 0.1 | 0.11 | 0.1 | 0.12 | 0.11 | 0.12 | 0.04 | 0.05 |
| His | 0.08 | 0.09 | 0.07 | 0.11 | 0.12 | 0.08 | 0.09 | 0.13 | 0.15 |
| Arg | 0.34 | 0.38 | 0.39 | 0.15 | 0.07 | 0.04 | 0.03 | 0.08 | 0.06 |
| Pro | 1.09 | 1.19 | 1.22 | 1.14 | 1.26 | 1.36 | 1.33 | 1.19 | 1.21 |
| Total | 8.79 | 9.15 | 9.26 | 9.16 | 10.07 | 11.36 | 11.3 | 10.27 | 10.62 |

There was observed a tendency that the succinic acid content was maximized at pH 6.8, and decreased as pH became higher from that value. Also for the glutamic acid content, the same tendency was observed. At pH 6.8, succinic acid and glutamic acid increased by 1.0% or more based on the dry weight of yeast. Glutamic acid exists upstream of succinic acid in the metabolic pathway. Therefore, it was estimated that the increase of succinic acid observed at pH 6.8 was provided by a certain origin substance existing upstream of glutamic acid, or by a pathway not including glutamic acid, and it was thought that possibility that glutamic acid is the origin substance of succinic acid is low.

Example 7: Influence of Temperature

In order to examine the optimal temperature conditions for generating succinic acid, experiments were performed under the same conditions as those of Example 4 except that pH was uncontrolled, treatment time was 3 hours, and the temperature was 40, 47, or 55° C.

The results are shown in the following table.

TABLE 7

| | | (%/Dry yeast weight) | | |
|---|---|---|---|---|
| | | Time | | |
| | 0 | | 3 | |
| Temperature | — | 40 | 47 | 55 |
| Citric acid | 0.90 | 0.87 | 0.42 | 0.22 |
| Malic acid | 0.13 | 0.17 | 0.12 | 0.18 |
| Succinic acid | 0.25 | 0.71 | 1.10 | 0.62 |
| Lactic acid | 0.06 | 0.23 | 0.37 | 0.14 |
| Acetic acid | 0.04 | 0.32 | 0.38 | 0.09 |
| Pyroglutamic acid | 0.34 | 0.28 | 0.26 | 0.22 |
| Asp | 1.24 | 1.01 | 0.52 | 0.81 |
| Thr | 0.25 | 0.27 | 0.28 | 0.29 |
| Ser | 0.18 | 0.13 | 0.16 | 0.23 |
| Glu | 3.99 | 3.77 | 4.24 | 5.02 |
| Gly | 0.14 | 0.19 | 0.23 | 0.27 |
| Ala | 0.52 | 0.57 | 0.59 | 0.57 |
| Cys | 0.27 | 0.29 | 0.31 | 0.32 |
| Val | 0.04 | 0.04 | 0.05 | 0.04 |
| Met | 0.01 | 0.01 | 0.02 | 0.02 |
| Ile | 0.22 | 0.24 | 0.25 | 0.27 |
| Leu | 0.16 | 0.17 | 0.20 | 0.23 |
| Tyr | 0.08 | 0.09 | 0.10 | 0.12 |
| Phe | 0.10 | 0.11 | 0.13 | 0.15 |
| Lys | 0.15 | 0.18 | 0.20 | 0.23 |
| His | 0.08 | 0.08 | 0.09 | 0.10 |
| Arg | 0.45 | 0.47 | 0.46 | 0.49 |
| Pro | 0.20 | 0.22 | 0.24 | 0.25 |
| Total | 8.09 | 7.85 | 8.07 | 9.40 |

The increase of succinic acid was most promoted at 47° C., whereas the increase of glutamic acid was most promoted at 55° C. At 55° C., glutamic acid increased, but increase of succinic acid was suppressed. On the basis of the fact that glutamic acid exists upstream of the succinic acid synthesis, and the results of this experiment, it was estimated that the synthesis of succinic acid at the time of the organic acid generation treatment occurs via glutamic acid, and the activity for the synthesis of succinic acid from glutamic acid decreases at 47° C. or higher temperature.

Example 8: Investigation of Treatment Time at Optimum pH and Temperature

The organic acid generation treatment was performed at the optimum pH (pH 6.8) and temperature (47° C.) found above. In order to measure change of ingredients at the time of the organic acid generation treatment, the experiment was performed under the same conditions as those of Example 4 except that the organic acid generation treatment time was extended to 30 hours.

The results are shown in the following table.

TABLE 8

| | | | | (%/Dry yeast weight) | |
|---|---|---|---|---|---|
| Time | 0 | 3 | 6 | 22 | 30 |
| Citric acid | 0.61 | 0.51 | 0.30 | 0.00 | 0.00 |
| Malic acid | 0.16 | 0.06 | 0.08 | 0.03 | 0.03 |
| Succinic acid | 0.54 | 1.72 | 2.10 | 2.79 | 2.88 |

TABLE 8-continued

| Time | 0 | 3 | 6 | 22 | 30 |
|---|---|---|---|---|---|
| | | | (%/Dry yeast weight) | | |
| Lactic acid | 0.07 | 0.14 | 0.10 | 0.00 | 0.00 |
| Acetic acid | 0.04 | 0.37 | 0.59 | 1.35 | 1.44 |
| Pyroglutamic acid | 0.60 | 0.34 | 0.29 | 0.39 | 0.32 |
| Asp | 0.79 | 0.41 | 0.22 | 0.17 | 0.26 |
| Thr | 0.75 | 0.35 | 0.29 | 0.28 | 0.31 |
| Ser | 0.10 | 0.07 | 0.06 | 0.06 | 0.07 |
| Glu | 4.46 | 5.06 | 5.22 | 5.36 | 5.58 |
| Gly | 0.13 | 0.19 | 0.21 | 0.28 | 0.33 |
| Ala | 1.44 | 1.50 | 1.48 | 1.51 | 1.56 |
| Cys | 0.10 | 0.10 | 0.12 | 0.18 | 0.18 |
| Val | 0.13 | 0.17 | 0.18 | 0.27 | 0.28 |
| Met | 0.02 | 0.03 | 0.03 | 0.03 | 0.03 |
| Ile | 0.09 | 0.11 | 0.11 | 0.15 | 0.15 |
| Leu | 0.04 | 0.06 | 0.06 | 0.10 | 0.11 |
| Tyr | 0.03 | 0.04 | 0.04 | 0.05 | 0.04 |
| Phe | 0.04 | 0.05 | 0.06 | 0.16 | 0.16 |
| Lys | 0.06 | 0.09 | 0.09 | 0.13 | 0.14 |
| His | 0.07 | 0.08 | 0.09 | 0.09 | 0.10 |
| Arg | 0.32 | 0.33 | 0.22 | 0.11 | 0.07 |
| Pro | 0.46 | 0.45 | 0.51 | 0.60 | 0.64 |
| Total | 9.03 | 9.09 | 8.99 | 9.53 | 10.01 |

The change was substantially no longer observed after the organic acid generation treatment for 22 hours, and it seemed that the reaction ended.

Example 9: Preparation of Yeast Extract

Yeast cells that had undergone the organic acid generation treatment were prepared under the same conditions as those of Example 8, except that the organic acid generation treatment was performed under the optimal conditions for increasing succinic acid and glutamic acid found above (pH 6.8, temperature of 47° C., treatment time of 6 hours), and subjected to the hot water extraction treatment to obtain a yeast extract.

The results are shown in the following table.

TABLE 9

| | Yeast suspension | | Yeast extract |
|---|---|---|---|
| Organic acid generation | (%/Dry yeast weight) | | (%/Dry |
| treatment time | 0 | 6 | yeast extract weight) |
| Citric acid | 0.45 | 0.10 | 0.32 |
| Malic acid | 0.23 | 0.10 | 0.41 |
| Succinic acid | 0.50 | 2.56 | 10.12 |
| Lactic acid | 0.09 | 0.66 | 3.70 |
| Acetic acid | 0.02 | 0.54 | 1.56 |
| Pyroglutamic acid | 0.76 | 0.37 | 1.17 |
| Asp | 0.59 | 0.19 | 0.72 |
| Thr | 0.66 | 0.39 | 1.28 |
| Ser | 0.16 | 0.10 | 0.42 |
| Glu | 4.35 | 5.55 | 21.43 |
| Gly | 0.08 | 0.20 | 0.77 |
| Ala | 1.18 | 1.32 | 5.25 |

TABLE 9-continued

| | Yeast suspension | | Yeast extract |
|---|---|---|---|
| Organic acid generation | (%/Dry yeast weight) | | (%/Dry |
| treatment time | 0 | 6 | yeast extract weight) |
| Cys | 0.11 | 0.13 | 0.40 |
| Val | 0.15 | 0.25 | 0.98 |
| Met | 0.02 | 0.03 | 0.11 |
| Ile | 0.12 | 0.16 | 0.62 |
| Leu | 0.05 | 0.08 | 0.33 |
| Tyr | 0.03 | 0.04 | 0.16 |
| Phe | 0.06 | 0.06 | 0.26 |
| Lys | 0.09 | 0.11 | 0.44 |
| His | 0.06 | 0.08 | 0.36 |
| Arg | 0.36 | 0.31 | 1.34 |
| Pro | 0.40 | 0.48 | 1.95 |
| Total | 8.47 | 9.48 | 36.84 |

A yeast extract containing 10.1% of succinic acid and 21.4% of glutamic acid could be prepared.

Example 10: Investigation with Different Strains

The above investigations were performed only for the *Saccharomyces cerevisiae* SC21 strain. Therefore, whether the increase of organic acid and amino acid ingredients obtained during the organic acid generation treatment elucidated above could be observed for other *Saccharomyces cerevisiae* strains and *Candida utilis* strains, and how much the contents thereof in yeast extracts would be were examined by using the following deposited strains.

That is, *Saccharomyces cerevisiae* FERM BP-8081, and FERM P-14013 strains, and *Candida utilis* NBRC619, NBCRC988, and NBRC1086 strains were used. The FERM BP-8081 and FERM P-14013 strains were cultured under the same conditions as those for the SC21 strain described above except that the feeding amount of molasses was adjusted so that molasses should be supplied neither too much nor too little. The *Candida utilis* strains were cultured under the same conditions as those for the SC21 strain except that the conditions of the starting medium for the main culture were changed as follows, and molasses was fed neither too much nor too little. Then, under the same conditions as those of Examples 8 and 9, the organic acid generation treatment was performed, and the obtained yeast cells were subjected to hot water extraction to obtain yeast extracts.

(Composition of Starting Medium)

| Urea | 30 g |
|---|---|
| Phosphoric acid | 5 ml |
| Magnesium sulfate heptahydrate | 0.3 g |
| Yeast extract | 1.2 g |

A total volume of 1.15 L was obtained by adding distilled water.

The results are shown in the following table.

TABLE 10

| | Yeast suspension (%/Dry yeast weight) | | | | | | | | | |
|---|---|---|---|---|---|---|---|---|---|---|
| | Accession No. of strain | | | | | | | | | |
| | FERM BP-8081 | | FERM P-14013 | | NBRC619 | | NBRC988 | | NBRC1086 | |
| | Genus and species | | | | | | | | | |
| | S. cerevisiae | | S. cerevisiae | | C. utilis | | C. utilis | | C. utilis | |
| Organic acid generation treatment time | Before treatment | After treatment for 6 H | Before treatment | After treatment for 6 H | Before treatment | After treatment for 6 H | Before treatment | After treatment for 6 H | Before treatment | After treatment for 6 H |
| Citric acid | 0.65 | 0.40 | 0.16 | 0.00 | 0.11 | 0.00 | 0.19 | 0.00 | 0.21 | 0.00 |
| Malic acid | 0.13 | 0.04 | 0.02 | 0.04 | 0.07 | 0.04 | 0.07 | 0.05 | 0.07 | 0.06 |
| Succinic acid | 0.39 | 1.50 | 0.19 | 1.44 | 0.21 | 0.61 | 0.28 | 1.27 | 0.20 | 1.32 |
| Lactic acid | 0.07 | 0.06 | 0.02 | 0.18 | 0.10 | 0.39 | 0.14 | 0.22 | 0.07 | 0.31 |
| Acetic acid | 0.01 | 0.45 | 0.04 | 0.53 | 0.10 | 0.45 | 0.12 | 0.64 | 0.04 | 0.55 |
| Pyroglutamic acid | 0.38 | 0.49 | 0.40 | 0.27 | 0.30 | 0.09 | 0.32 | 0.08 | 0.28 | 0.07 |
| Asp | 0.19 | 0.14 | 1.45 | 0.81 | 0.13 | 0.18 | 0.24 | 0.11 | 0.11 | 0.09 |
| Thr | 0.08 | 0.15 | 0.39 | 0.40 | 0.11 | 0.13 | 0.14 | 0.14 | 0.15 | 0.08 |
| Ser | 0.07 | 0.15 | 0.38 | 0.24 | 0.07 | 0.06 | 0.07 | 0.07 | 0.06 | 0.05 |
| Glu | 3.34 | 3.86 | 3.24 | 3.59 | 1.68 | 1.88 | 2.10 | 2.13 | 2.27 | 2.43 |
| Gly | 0.11 | 0.26 | 0.16 | 0.34 | 0.07 | 0.13 | 0.05 | 0.13 | 0.03 | 0.10 |
| Ala | 0.67 | 0.81 | 0.75 | 0.82 | 0.61 | 1.47 | 0.64 | 2.14 | 0.67 | 1.92 |
| Cys | 0.11 | 0.05 | 0.09 | 0.10 | 0.04 | 0.17 | 0.04 | 0.35 | 0.05 | 0.28 |
| Val | 0.06 | 0.18 | 0.28 | 0.32 | 0.14 | 0.16 | 0.12 | 0.14 | 0.11 | 0.13 |
| Met | 0.00 | 0.03 | 0.02 | 0.04 | 0.01 | 0.01 | 0.02 | 0.02 | 0.02 | 0.02 |
| Ilo | 0.31 | 0.37 | 0.21 | 0.25 | 0.09 | 0.11 | 0.09 | 0.10 | 0.05 | 0.06 |
| Leu | 0.03 | 0.13 | 0.17 | 0.22 | 0.07 | 0.10 | 0.08 | 0.10 | 0.05 | 0.06 |
| Tyr | 0.03 | 0.08 | 0.09 | 0.12 | 0.08 | 0.09 | 0.07 | 0.07 | 0.05 | 0.06 |
| Phe | 0.04 | 0.11 | 0.13 | 0.16 | 0.08 | 0.10 | 0.09 | 0.13 | 0.07 | 0.11 |
| Lys | 0.07 | 0.17 | 0.28 | 0.33 | 0.19 | 0.15 | 0.23 | 0.10 | 0.19 | 0.10 |
| His | 0.05 | 0.07 | 0.12 | 0.16 | 0.13 | 0.15 | 0.10 | 0.12 | 0.08 | 0.11 |
| Arg | 0.85 | 0.98 | 0.61 | 0.52 | 0.32 | 0.13 | 0.28 | 0.23 | 0.43 | 0.30 |
| Pro | 0.00 | 0.08 | 0.00 | 0.00 | 0.00 | 0.00 | 0.00 | 0.00 | 0.00 | 0.00 |
| Total | 6.01 | 7.62 | 8.37 | 8.42 | 3.82 | 5.02 | 4.36 | 6.08 | 4.39 | 5.90 |

| Organic acid generation treatment time | Yeast extract (%/Dry yeast extract weight) | | | | |
|---|---|---|---|---|---|
| | FT4 | YF | NBRC619 | NBRC988 | NBRC1086 |
| Citric acid | 1.29 | 0.21 | 0.13 | 0.11 | 0.19 |
| Malic acid | 0.15 | 0.13 | 0.12 | 0.15 | 0.21 |
| Succinic acid | 6.83 | 5.34 | 2.00 | 4.19 | 5.55 |
| Lactic acid | 0.42 | 0.72 | 1.24 | 0.75 | 1.22 |
| Acetic acid | 1.99 | 1.97 | 1.46 | 2.06 | 2.25 |
| Pyroglutamic acid | 1.23 | 0.90 | 0.13 | 0.11 | 0.19 |
| Asp | 0.59 | 3.08 | 0.67 | 0.54 | 0.51 |
| Thr | 0.56 | 1.31 | 0.39 | 1.56 | 0.38 |
| Ser | 0.67 | 1.00 | 0.22 | 0.26 | 0.22 |
| Glu | 15.46 | 13.86 | 6.29 | 7.46 | 9.38 |
| Gly | 1.09 | 1.31 | 0.45 | 0.45 | 0.40 |
| Ala | 3.33 | 3.26 | 5.01 | 7.45 | 7.65 |
| Cys | 0.20 | 0.31 | 0.48 | 2.10 | 3.08 |
| Val | 0.81 | 1.25 | 0.55 | 0.51 | 0.60 |
| Met | 0.14 | 0.15 | 0.04 | 0.07 | 0.16 |
| Ilo | 1.56 | 0.97 | 0.38 | 0.37 | 0.24 |
| Leu | 0.60 | 0.91 | 0.32 | 0.40 | 0.25 |
| Tyr | 0.35 | 0.48 | 0.24 | 0.26 | 0.23 |
| Phe | 0.50 | 0.70 | 0.32 | 0.61 | 0.48 |
| Lys | 0.75 | 1.32 | 0.47 | 0.38 | 0.39 |
| His | 0.29 | 0.72 | 0.51 | 0.42 | 0.38 |
| Arg | 3.81 | 2.25 | 0.53 | 1.00 | 1.12 |
| Pro | 0.27 | 0.00 | 0.00 | 0.00 | 0.00 |
| Total | 30.98 | 32.90 | 16.87 | 23.84 | 25.47 |

Example 11: Preparation and Evaluation of Paste of Yeast Extract

In order to perform organoleptic evaluation of yeast extract, a yeast extract was obtained in the same manner as that of Example 9. The obtained yeast extract was concentrated by using an evaporator to prepare a paste of the yeast extract.

As a result, a yeast extract paste containing 4.31% of succinic acid, 8.6% of glutamic acid (henceforth indicated as Glu), and 0.17% of nucleic acids (in terms of disodium IMP heptahydrate (henceforth indicated as I) and disodium GMP heptahydrate (henceforth indicated as G), and these are henceforth indicated as I+G) was obtained.

<Confirmation of Synergistic Effect of Trial Product>

The following experiments were conducted in order to verify whether umami exhibited by synergistic effect of I+G and substance other than Glu could be obtained with the above trial product yeast extract.

A diluted solution containing 0.2% (solid content) of the trial product yeast extract was prepared, and two types of simulation solutions (containing umami ingredients in amounts corresponding to those in the diluted solution containing 0.2% of the yeast extract) were prepared by using reagents. Na was adjusted with NaCl, and K was adjusted with $KH_2PO_4$.

Simulation solution (1): Solution containing Glu and I+G

Simulation solution (2): Solution containing organic acid, amino acid, I+G, Na, and K Then, contents of the umami ingredients in the simulation solutions (1) and (2) (succinic acid, Glu, I+G, provided that the simulation solution (1) did not contain succinic acid) were changed to 50%, 75%, 125%, and 150% (the amounts contained in the trial product yeast extract were taken as 100%) to prepare simulation solutions of different umami intensities. The details of the simulation solutions are shown in the following table.

TABLE 11-1

| | Simulation solution (1) type | | | | | Simulation solution (2) type | | | | | (mg/100 g) |
|---|---|---|---|---|---|---|---|---|---|---|---|
| | Amount corresponding to those in 0.2% yeast extract | | | | | | | | | | |
| | 50% | 75% | 100% | 125% | 150% | 50% | 75% | 100% | 125% | 150% | |
| Succinic acid | | | | | | 4828 | 7243 | 9657 | 12071 | 14485 | |
| Disodium GMP hydrate (G) | 151 | 227 | 303 | 379 | 454 | 151 | 227 | 303 | 379 | 454 | |
| Disodium IMP hydrate (I) | 9 | 13 | 17 | 22 | 26 | 9 | 13 | 17 | 22 | 26 | |
| Glu | 9610 | 14415 | 19221 | 24026 | 28831 | 9610 | 14415 | 19221 | 24026 | 28831 | |
| Minerals | | | | | | | | | | | |
| Na | | | | | | 5126 | 5126 | 5126 | 5126 | 5126 | |
| K | | | | | | 8319 | 8320 | 8321 | 8322 | 8323 | |
| Organic acids other than succinic acid | | | | | | | | | | | |
| Citric acid | | | | | | 1249 | 1249 | 1249 | 1249 | 1249 | |
| Malic acid | | | | | | 169 | 169 | 169 | 169 | 169 | |
| Lactic acid | | | | | | 1080 | 1080 | 1080 | 1080 | 1080 | |
| Acetic acid | | | | | | 2880 | 2880 | 2880 | 2880 | 2880 | |
| Pyroglutamic acid | | | | | | 2329 | 2329 | 2329 | 2329 | 2329 | |
| Amino acids other than glutamic acid | | | | | | | | | | | |
| Asp | | | | | | 406 | 406 | 406 | 406 | 406 | |
| Thr | | | | | | 339 | 339 | 339 | 339 | 339 | |
| Ser | | | | | | 110 | 110 | 110 | 110 | 110 | |
| Gly | | | | | | 1126 | 1126 | 1126 | 1126 | 1126 | |
| Ala | | | | | | 3133 | 3133 | 3133 | 3133 | 3133 | |
| Cys | | | | | | 491 | 491 | 491 | 491 | 491 | |
| Val | | | | | | 847 | 847 | 847 | 847 | 847 | |
| Met | | | | | | 76 | 76 | 76 | 76 | 76 | |
| Iso | | | | | | 618 | 618 | 618 | 618 | 618 | |
| Leu | | | | | | 389 | 389 | 389 | 389 | 389 | |
| Tyr | | | | | | 93 | 93 | 93 | 93 | 93 | |
| Phe | | | | | | 288 | 288 | 288 | 288 | 288 | |
| Lys | | | | | | 398 | 398 | 398 | 398 | 398 | |
| His | | | | | | 279 | 279 | 279 | 279 | 279 | |
| Arg | | | | | | 1067 | 1067 | 1067 | 1067 | 1067 | |
| Pro | | | | | | 2227 | 2227 | 2227 | 2227 | 2227 | |

Umami intensities of the prepared simulation solutions of different types and the 0.2% aqueous solution of the trial product were evaluated, and whether there was synergistic effect of umami ingredient other than glutamic acid and I+G, and whether umami was enhanced were evaluated by organoleptic evaluation.

Evaluation Method:

The evaluation results were indicated with umami intensity scores ranging from 1 to 10 with increments of 0.5. The evaluation result for a sample containing umami ingredients used for the simulation solution (2) in amounts corresponding to those of 100% of the yeast extract is graded to be umami intensity of 5.

Evaluators: 13 Trained Panelists

The results are shown in the following table and FIG. 1.

TABLE 11-2

| Umami intensity | | | | | (Maximum score: 10) |
|---|---|---|---|---|---|
| Amount corresponding to those in 0.2% yeast extract | 50.00% | 75.00% | 100.00% | 125.00% | 150.00% |
| Simulation solution (1) type | 1.9 | 2.4 | 3.1 | 3.8 | 5.2 |
| Simulation solution (2) type | 2.9 | 3.7 | 5.0 | 6.7 | 9.6 |
| Umami intensity | | | | | |
| 0.2% Diluted solution of the trial product yeast extract | 5.2 | | | | |
| | | 75%/50% | 100%/75% | 125%/100% | 150%/125% |
| Increasing ratio for simulation solution (1) type | | 1.26 | 1.27 | 1.25 | 1.36 |
| Increasing ratio for simulation solution (2) type | | 1.29 | 1.34 | 1.35 | 1.42 |

With the simulation solution (1), the umami intensity was synergistically increased, and the synergistic effect of glutamic acid and I+G for umami was detected as previously reported. On the other hand, with the simulation solution (2), the umami intensity was markedly enhanced compared with that provided by the simulation solution (1). The umami intensity provided by the 0.2% solution of the trial product yeast extract was higher than that provided by the 100% content type simulation solution (2), and thus existence of enhancement of umami by an ingredient not contained in the simulation solution was demonstrated.

As for the reason for the higher umami intensity of the simulation solution (2), it is considered that it was because the simulation solution (2) contained succinic acid, which is an umami ingredient. However, because the umami intensity of the simulation solution (2) was further synergistically increased compared with that provided by the simulation solution (1), it was demonstrated that there was exerted a synergistic effect of I+G and umami ingredient other than glutamic acid in the simulation solution (2). On the basis of the above, a synergistic effect for umami other than the synergistic effect of I+G and Glu for umami can be expected for the trial product yeast extract.

Example 12: Investigation of Taste-Improving Effect 1

There were prepared test samples containing each of the yeast extracts and simulation solution in which umami ingredients contained in yeast extract were reconstructed with regents in an amount of 0.01% (in terms of dry yeast extract weight) or such an amount that concentrations of the reagents correspond to those of umami ingredients contained in yeast extract mentioned as (1) to (8) in the following table in a 2.0% hot water-diluted solution of fumet de poisson produced by Mascot Foods.

TABLE 12-1

| | Ingredient | Amount (mg) |
|---|---|---|
| Mineral | Na | 5126 |
| | K | 8319 |
| Organic acid | Citric acid | 1249 |
| | Malic acid | 169 |
| | Succinic acid | 9657 |
| | Lactic acid | 1080 |
| | Acetic acid | 2880 |
| | Pyroglutamic acid | 2329 |
| Free Amino acid | Asp | 406 |
| | Thr | 339 |
| | Ser | 110 |
| | Glu | 19221 |

TABLE 12-1-continued

| | Ingredient | Amount (mg) |
|---|---|---|
| | Gly | 1126 |
| | Ala | 3133 |
| | Cys | 491 |
| | Val | 847 |
| | Met | 76 |
| | Iso | 618 |
| | Leu | 389 |
| | Tyr | 93 |
| | Phe | 288 |
| | Lys | 398 |
| | His | 279 |
| | Arg | 1067 |
| | Pro | 2227 |
| Nucleic acid | Imp-Na$_2$•7H$_2$O | 303 |
| | Gmp-Na$_2$•7H$_2$O | 17 |

The raw materials were weighed, and dissolved in distilled water, and the total weight was adjusted to 100 g with distilled water.

The samples were evaluated by 13 trained panelists through test drinking of the samples, and graded by them for favorableness of seafood flavor, and intensity of taste.

(Organoleptic Evaluation Criteria)

Intensity of seafood flavor was graded in comparison with that of blank (2.0% hot water diluted solution not containing yeast extract etc.), of which score was 3, as follows: 1=very weak seafood flavor, 2=weak seafood flavor, 4=strong seafood flavor, and 5=very strong seafood flavor.

Intensity of taste was graded in comparison with that of the blank, of which score was 3, as follows: 1=very weak taste, 2=weak taste, 4=strong taste, and 5=very strong taste.

The results are shown in the following table and FIG. 2.

TABLE 12-2

| | Favorableness of seafood flavor | Intensity of taste |
|---|---|---|
| (1) Trial yeast extract of the invention | 4.4 | 4.5 |
| (2) Commercial yeast extract A | 3.4 | 4.0 |
| (3) Commercial yeast extract B | 3.2 | 4.6 |
| (4) Commercial yeast extract C | 3.3 | 3.4 |

TABLE 12-2-continued

|  | Favorableness of seafood flavor | Intensity of taste |
|---|---|---|
| (5) Commercial yeast extract D | 3.2 | 3.6 |
| (6) Commercial yeast extract E | 3.2 | 3.7 |
| (7) Commercial yeast extract F | 3.2 | 3.0 |
| (8) Simulation yeast extract | 4.0 | 4.0 |

(2) HIMAX GL (Fuji Foods),
(3) Vertex IG20 (Fuji Foods),
(4) Yeast Extract 21-TFP-S (Fuji Foods),
(5) glutamic acid-enriched yeast extract 1 of another company,
(6) glutamic acid-enriched yeast extract 2 of another company,
(7) autolysis type yeast extract 3 of another company The trial product yeast extract of the present invention having higher contents of succinic acid and glutamic acid compared with the commercial yeast extracts markedly enhanced seafood flavor, and strengthened taste. The measured values of the ingredients of the used yeast extracts are summarized in the following table.

TABLE 12-3

| | (mg/Dry yeast extract weight 100 g) | | | | | |
|---|---|---|---|---|---|---|
| | Total amino acid | Glutamic acid | Nucleic acid | Succinic acid | Acetic acid | Lactic acid |
| (1) Trial yeast extract of the invention | 31108 | 19221 | 320 | 9657 | 2880 | 1080 |
| (2) Commercial yeast extract A | 27874 | 15481 | 2114 | 1773 | 517 | 775 |
| (3) Commercial yeast extract B | 12070 | 5966 | 20293 | 1324 | 188 | 13 |
| (4) Commercial yeast extract C | 5666 | 1803 | 2461 | 250 | 80 | 820 |
| (5) Commercial yeast extract D | 24348 | 17437 | 232 | 736 | 145 | 822 |
| (6) Commercial yeast extract E | 28230 | 18123 | 3535 | 283 | 477 | 997 |
| (7) Commercial yeast extract F | 41827 | 2286 | 15 | 805 | 409 | 390 |

Example 13: Investigation of Taste-Improving Effect 2

There were prepared samples containing 0.05% at the time of ingestion of the same yeast extracts and simulation yeast extract as those used in Example 12 ((1) to (8)) in a 2.0% hot water diluted solution of chicken soup powder (having the composition shown in the following table).

TABLE 13-1

| Chicken soup powder | Weight % |
|---|---|
| Very-refined sugar | 20.00 |
| Chicken extract powder | 11.50 |
| Powdered soy sauce | 7.00 |
| Onion extract powder | 3.00 |
| Garlic powder | 1.00 |
| White pepper | 0.20 |
| Salt | 16.50 |
| Dextrin | 40.80 |
| Total | 100.00 |

The samples were evaluated by 13 trained panelists through test drinking of the samples, and graded by them for intensity of initial taste, intensity of richness, and intensity of taste.

(Organoleptic Evaluation Criteria)

Intensity of initial taste was graded in comparison with that of blank, of which score is 3, as follows: 1=very weak initial taste, 2=weak initial taste, 4=strong initial taste, and 5=very strong initial taste.

Intensity of richness was graded in comparison with that of blank, of which score is 3, as follows: 1=very weak richness, 2=weak richness, 4=strong richness, and 5=very strong richness.

Intensity of taste was graded in comparison with that of the blank, of which score was 3, as follows: 1=very weak taste, 2=weak taste, 4=strong taste, and 5=very strong taste.

The results are shown in the following table.

TABLE 13-2

|  | Intensity of initial taste | Intensity of richness | Intensity of taste |
|---|---|---|---|
| (1) Trial yeast extract of the invention | 4.6 | 4.3 | 4.5 |
| (2) Commercial yeast extract A | 3.8 | 4.2 | 4.0 |
| (3) Commercial yeast extract B | 3.5 | 4.6 | 4.7 |
| (4) Commercial yeast extract C | 3.2 | 3.6 | 3.4 |
| (5) Commercial yeast extract D | 3.8 | 3.6 | 3.8 |
| (6) Commercial yeast extract E | 3.7 | 3.7 | 3.7 |
| (7) Commercial yeast extract F | 3.0 | 3.1 | 2.9 |
| (8) Simulation yeast extract | 3.8 | 3.7 | 3.9 |

By the addition of the trial product yeast extract, initial taste was markedly enhanced, richness was increased, and taste was also enhanced.

Example 14: Investigation of Urea Amount

The *Saccharomyces cerevisiae* SC21 strain was cultured to obtain yeast cells, and a yeast suspension prepared by using the obtained yeast cells was subjected to the organic acid generation treatment. In this investigation, how the amount of urea supplied at the time of the culture affects change of ingredients caused by the organic acid generation treatment was verified.

The experimental conditions are shown in the following table.

TABLE 14-1

| Step | Detailed conditions |
|---|---|
| Preculture | Medium: YPD liquid medium<br>Temperature: 30° C.<br>Revolving speed of rotary shaker: 200 rpm<br>Culture period: 24 hours |
| ↓ | |
| Main culture | Medium: 20, 13, 11, or 9.5 g of urea, 1.5 ml of phosphoric acid, 0.3 g of magnesium sulfate heptahydrate, 1.2 g of yeast extract; total volume of 1.15 L was obtained with distilled water<br>Inoculation amount: 50 ml of yeast suspension (dry yeast weight, 5 g)<br>Temperature: 32° C.<br>Aeration: 1.7 L/minute<br>Stirring speed: 650 rpm<br>KLa at the end of the culture: 500 hr$^{-1}$<br>pH Control: 4.5 as the lowest pH (adjusted by addition of 15% sodium carbonate)<br>Feed medium: Molasses (sugar content, 43%); volume, 500 ml<br>Culture period: 15 hours |
| ↓ | |
| Collection and washing of cells | Centrifugal separation (→ obtain cells for organic acid generation treatment) |
| ↓ | |
| Organic acid generation treatment | Temperature: 48° C.<br>Time: 5 hours<br>pH control: pH 6.8 (fixed)<br>Stirring: Stirred (with stirrer bar)<br>Dry yeast weight (solid content): 15% |

The results are shown in the following table.

TABLE 14-2

| | (%/Dry yeast weight) Intracellular nitrogen at the end of culture | | | | | | | |
|---|---|---|---|---|---|---|---|---|
| | 7.8% | | 7.6 | | 7.0 | | 6.0 | |
| | Urea amount at the time of culture | | | | | | | |
| | 20 g | | 13 g | | 11 g | | 9.5 g | |
| Time | 0 | 5 | 0 | 5 | 0 | 5 | 0 | 5 |
| Phosphoric acid | 1.16 | 1.60 | 1.20 | 1.63 | 1.14 | 1.48 | 1.27 | 1.60 |
| Citric acid | 0.68 | 0.33 | 0.65 | 0.21 | 1.04 | 0.55 | 1.53 | 0.74 |
| Malic acid | 0.15 | 0.10 | 0.16 | 0.13 | 0.21 | 0.18 | 0.30 | 0.15 |
| Succinic acid | 0.89 | 2.43 | 1.04 | 2.66 | 1.05 | 3.04 | 1.26 | 3.14 |
| Lactic acid | 0.10 | 0.25 | 0.13 | 0.44 | 0.16 | 0.68 | 0.25 | 0.92 |
| Acetic acid | 0.05 | 0.46 | 0.04 | 0.42 | 0.05 | 0.41 | 0.03 | 0.40 |
| Pyroglutamic acid | 0.55 | 0.41 | 0.52 | 0.32 | 0.24 | 0.24 | 0.09 | 0.22 |
| Asp | 0.08 | 0.07 | 0.05 | 0.07 | 0.06 | 0.03 | 0.07 | 0.01 |
| Thr | 0.96 | 0.51 | 0.81 | 0.37 | 0.38 | 0.33 | 0.15 | 0.22 |
| Ser | 0.13 | 0.11 | 0.12 | 0.10 | 0.17 | 0.12 | 0.19 | 0.16 |
| Glu | 5.71 | 6.39 | 5.18 | 5.96 | 3.83 | 3.53 | 2.90 | 2.49 |
| Gly | 0.14 | 0.21 | 0.12 | 0.20 | 0.11 | 0.18 | 0.09 | 0.14 |
| Ala | 1.25 | 1.31 | 1.09 | 1.18 | 0.49 | 0.58 | 0.38 | 0.56 |
| Cys | 0.22 | 0.24 | 0.24 | 0.27 | 0.21 | 0.27 | 0.26 | 0.36 |
| Val | 0.16 | 0.27 | 0.17 | 0.31 | 0.17 | 0.26 | 0.17 | 0.26 |
| Met | 0.00 | 0.08 | 0.00 | 0.04 | 0.01 | 0.02 | 0.01 | 0.03 |
| Ile | 0.19 | 0.26 | 0.18 | 0.20 | 0.16 | 0.17 | 0.18 | 0.17 |
| Leu | 0.07 | 0.11 | 0.07 | 0.10 | 0.08 | 0.10 | 0.10 | 0.10 |
| Tyr | 0.05 | 0.07 | 0.05 | 0.05 | 0.06 | 0.08 | 0.06 | 0.06 |
| Phe | 0.07 | 0.08 | 0.07 | 0.06 | 0.07 | 0.07 | 0.07 | 0.06 |
| Lys | 0.08 | 0.10 | 0.08 | 0.10 | 0.10 | 0.08 | 0.10 | 0.07 |
| His | 0.06 | 0.07 | 0.06 | 0.08 | 0.06 | 0.07 | 0.06 | 0.07 |
| Arg | 0.35 | 0.34 | 0.38 | 0.30 | 0.32 | 0.27 | 0.25 | 0.22 |
| Pro | 0.41 | 0.41 | 0.46 | 0.49 | 0.25 | 0.26 | 0.17 | 0.17 |
| Total | 9.93 | 10.63 | 9.13 | 9.88 | 6.53 | 6.42 | 5.21 | 5.15 |

By reducing urea supplied at the time of the culture, amount of succinic acid observed before the organic acid generation treatment was increased, and increase of the amount of succinic acid during the organic acid generation treatment was also promoted. On the other hand, when the cultured was performed under low urea conditions, amount of glutamic acid observed at the end of the culture was decreased, and the increase provided by the organic acid generation treatment was suppressed or reduced. The intracellular nitrogen amount at the end of the culture was decreased in a supplied urea amount-dependent manner. On the basis of these results, it was estimated that reduction of nitrogen supplied at the time of the culture reduced the intracellular nitrogen, thus conversion from carbon compounds such as saccharides and aliphatic acids to nitrogen compounds such as amino acids became difficult to advance, and the decrease of glutamic acid amount and the increase of the succinic acid amount were caused as a result.

Example 15: Investigation of Intracellular Nitrogen Amount

The Saccharomyces cerevisiae SC21 strain was cultured as the yeast, and a yeast cell suspension prepared by using the obtained yeast cells was subjected to the organic acid generation treatment. In this investigation, intracellular nitrogen amount observed at the end of the culture optimal to maximize amount of succinic acid generated by the organic acid generation treatment was investigated by changing the amount of urea.

The experimental conditions were the same as those of Example 14 except that the nitrogen amount in the medium for the main culture was changed to 11 g or 9 g.

The results are shown in the following table.

TABLE 15

| | (%/Dry yeast weight) Intracellular nitrogen at the end of culture | | | | | |
|---|---|---|---|---|---|---|
| | 6.8 | | | 5.5 | | |
| | Urea amount at the time of culture | | | | | |
| | 11 g | | | 9 g | | |
| Time | 0 | 3 | 5 | 0 | 3 | 5 |
| Phosphoric acid | 1.07 | 1.37 | 1.49 | 1.10 | 1.36 | 1.51 |
| Citric acid | 1.19 | 0.88 | 0.61 | 1.58 | 1.09 | 0.64 |
| Malic acid | 0.25 | 0.16 | 0.14 | 0.30 | 0.13 | 0.09 |
| Succinic acid | 1.11 | 2.50 | 3.00 | 0.94 | 1.89 | 2.25 |
| Lactic acid | 0.15 | 1.01 | 1.05 | 0.18 | 2.15 | 2.62 |
| Acetic acid | 0.04 | 0.31 | 0.46 | 0.05 | 0.24 | 0.33 |
| Pyroglutamic acid | 0.16 | 0.25 | 0.27 | 0.09 | 0.15 | 0.17 |
| Asp | 0.19 | 0.05 | 0.03 | 0.20 | 0.03 | 0.05 |
| Thr | 0.37 | 0.39 | 0.29 | 0.21 | 0.23 | 0.23 |
| Ser | 0.26 | 0.17 | 0.14 | 0.20 | 0.13 | 0.13 |
| Glu | 5.34 | 4.90 | 4.31 | 2.89 | 2.45 | 2.18 |
| Gly | 0.14 | 0.23 | 0.22 | 0.07 | 0.17 | 0.18 |
| Ala | 0.68 | 0.81 | 0.72 | 0.61 | 0.74 | 0.64 |
| Cys | 0.28 | 0.37 | 0.36 | 0.24 | 0.34 | 0.40 |
| Val | 0.19 | 0.32 | 0.31 | 0.24 | 0.32 | 0.29 |
| Met | 0.01 | 0.03 | 0.06 | 0.03 | 0.07 | 0.07 |
| Ile | 0.20 | 0.22 | 0.19 | 0.20 | 0.21 | 0.17 |
| Leu | 0.12 | 0.15 | 0.14 | 0.14 | 0.16 | 0.14 |
| Tyr | 0.10 | 0.09 | 0.11 | 0.14 | 0.12 | 0.11 |
| Phe | 0.11 | 0.08 | 0.12 | 0.11 | 0.13 | 0.11 |
| Lys | 0.13 | 0.13 | 0.10 | 0.22 | 0.18 | 0.11 |
| His | 0.07 | 0.09 | 0.09 | 0.06 | 0.07 | 0.07 |
| Arg | 0.41 | 0.41 | 0.30 | 0.23 | 0.24 | 0.20 |
| Pro | 0.33 | 0.36 | 0.35 | 0.16 | 0.18 | 0.21 |
| Total | 8.93 | 8.8 | 7.84 | 5.95 | 5.77 | 5.29 |

By increasing or decreasing the amount of urea to be supplied, intracellular nitrogen amount observed at the end of the culture was controlled to be 6.8% or 5.5%. As a result, when the intracellular nitrogen amount was 6.8%, succinic acid was significantly more increased. Glutamic acid was also more increased when the amount was 6.8%. On the basis of these results together with the results of Example 14, it was found that the intracellular nitrogen amount at the end of culture optimal to increase succinic acid is 6.0 to 7.0%.

Example 16: Investigation of Organic Acid Generation Treatment Time

The yeast cells of which intracellular nitrogen amount at the end of the culture was made to be 6.0 to 7.0% by reducing the amount of urea to be supplied generated a large amount of succinic acid as a result of the organic acid generation treatment, and it was estimated that the succinic acid generation had not terminated during the organic acid generation treatment for 5 hours. Then, it was verified whether a further larger amount of succinic acid could be obtained by prolonging the organic acid generation treatment time.

The experimental conditions were the same as those of Example 14 except that the nitrogen amount in the medium for the main culture was changed to 11 g, and the organic acid generation treatment time was changed to 28 hours.

The results are shown in the following table.

TABLE 16

| | (%/Dry yeast weight) | | | | | |
|---|---|---|---|---|---|---|
| | Intracellular nitrogen at the end of culture | | | | | |
| | 6.7 | | | | | |
| | Urea amount at the time of culture | | | | | |
| | 11 g | | | | | |
| | Organic acid generation treatment time | | | | | |
| | 0 | 3 | 5 | 7 | 23 | 28 |
| Phosphoric acid | 1.14 | 1.67 | 1.86 | 1.93 | 2.15 | 2.20 |
| Citric acid | 1.29 | 0.99 | 0.59 | 0.18 | 0.00 | 0.00 |
| Malic acid | 0.32 | 0.23 | 0.19 | 0.12 | 0.03 | 0.03 |
| Succinic acid | 0.98 | 2.91 | 3.47 | 3.93 | 4.09 | 4.08 |
| Lactic acid | 0.11 | 0.65 | 0.64 | 0.48 | 0.61 | 0.46 |
| Acetic acid | 0.02 | 0.31 | 0.46 | 0.60 | 1.78 | 2.20 |
| Pyroglutamic acid | 0.08 | 0.21 | 0.23 | 0.22 | 0.18 | 0.18 |

With a treatment time longer than 7 hours, the increase rate of succinic acid reduced. Even if the treatment time is longer than 7 hours, succinic acid does not substantially increase, but possibility of bacterial proliferation increases, and therefore it was considered that the optimal organic acid generation treatment time is about 7 to 9 hours.

Example 17: Preparation of Yeast Extract

Yeast cells were cultured by adjusting the nitrogen amount to be supplied so that the nitrogen amount based on the cells at the end of the culture should be 6.0 to 7.0%, the obtained yeast cells were subjected to the organic acid generation treatment, and a yeast extract was prepared.

The experimental conditions are shown in the following table.

TABLE 17-1

| Step | Detailed conditions |
|---|---|
| Preculture | Medium: YPD liquid medium<br>Temperature: 30° C.<br>Revolving speed of rotary shaker: 200 rpm<br>Culture period: 24 hours |
| ↓ | |
| Main culture | Medium: 11 g of urea, 1.5 ml of phosphoric acid, 0.3 g of magnesium sulfate heptahydrate, 1.2 g of yeast extract; total volume of 1.15 L was obtained with distilled water<br>Inoculation amount: 50 ml of yeast suspension (dry yeast weight, 5 g)<br>Temperature: 32° C.<br>Aeration: 1.7 L/minute<br>Stirring speed: 650 rpm |

TABLE 17-1-continued

| Step | Detailed conditions |
|---|---|
| | KLa at the end of the culture: 500 hr$^{-1}$<br>pH Control: 4.5 as the lowest pH (adjusted by addition of 15% sodium carbonate)<br>Feed medium: Molasses (sugar content, 43%); volume, 500 ml<br>Culture period: 15 hours |
| ↓ | |
| Collection and washing of cells | Centrifugal separation (→ obtain cells for organic acid generation treatment) |
| ↓ | |
| Organic acid generation treatment | Temperature: 48° C.<br>Time: 7 hours<br>pH control: pH 6.8 (fixed)<br>Stirring: Stirred (with stirrer bar)<br>Dry yeast weight (solid content): 15% |
| ↓ | |
| Hot water extraction treatment | Temperature: 85° C.<br>Time: 30 minutes |
| ↓ | |
| Removal of insoluble matter | Centrifugation |

The results are shown in the following table.

TABLE 17-2

| | Yeast suspension (%/Dry yeast weight) | | | | |
|---|---|---|---|---|---|
| Intracellular nitrogen at the end of culture | 6.6 | | | | |
| | (%/Dry yeast weight) 11 g | | | | Yeast extract (%/Dry yeast |
| Urea amount at the time of culture | | | | | extract weight) |
| Organic acid generation treatment time | 0 | 3 | 5 | 7 | |
| Phosphoric acid | 1.07 | 1.44 | 1.56 | 2.19 | 7.39 |
| Citric acid | 1.44 | 1.14 | 0.81 | 0.00 | 0.30 |
| Malic acid | 0.36 | 0.27 | 0.24 | 0.21 | 0.60 |
| Succinic acid | 0.77 | 2.76 | 3.46 | 4.15 | 14.23 |
| Lactic acid | 0.08 | 0.47 | 0.46 | 0.68 | 1.90 |
| Acetic acid | 0.02 | 0.30 | 0.46 | 0.60 | 2.04 |
| Pyroglutamic acid | 0.11 | 0.20 | 0.26 | 0.31 | 0.69 |
| Asp | 0.09 | 0.02 | 0.02 | 0.05 | 0.12 |
| Thr | 0.23 | 0.17 | 0.15 | 0.16 | 1.01 |
| Ser | 0.23 | 0.15 | 0.13 | 0.13 | 0.45 |
| Glu | 3.39 | 3.17 | 3.13 | 3.19 | 10.61 |
| Gly | 0.11 | 0.18 | 0.19 | 0.21 | 0.67 |
| Ala | 0.31 | 0.47 | 0.49 | 0.51 | 1.66 |
| Cys | 0.21 | 0.27 | 0.29 | 0.29 | 0.93 |
| Val | 0.14 | 0.24 | 0.24 | 0.25 | 0.82 |
| Met | 0.05 | 0.04 | 0.03 | 0.00 | 0.19 |
| Ile | 0.38 | 0.33 | 0.28 | 0.31 | 1.00 |
| Leu | 0.07 | 0.07 | 0.06 | 0.07 | 0.26 |
| Tyr | 0.03 | 0.02 | 0.04 | 0.04 | 0.14 |
| Phe | 0.05 | 0.03 | 0.05 | 0.04 | 0.14 |
| Lys | 0.09 | 0.06 | 0.05 | 0.05 | 0.15 |
| His | 0.04 | 0.05 | 0.05 | 0.05 | 0.16 |
| Arg | 0.24 | 0.22 | 0.20 | 0.18 | 0.56 |
| Pro | 0.22 | 0.25 | 0.26 | 0.28 | 0.92 |
| Total | 5.88 | 5.74 | 5.66 | 5.78 | 19.78 |

The reduction of the nitrogen amount at the end of culture attained by reducing the amount of nitrogen supplied at the time of the culture significantly increased succinic acid in the yeast extract.

Example 18: Investigation in Bench Scale

Since the experiments described above were performed in a laboratory scale, the preparation method was also investigated in a bench scale for actual production.

The *Saccharomyces cerevisiae* SC21 strain was cultured as the yeast, and a yeast cell suspension prepared by using the obtained yeast cells was subjected to the organic acid generation treatment. Then, through filtration and concentration treatments, a yeast extract was prepared.

The experimental conditions are shown below.
<Yeast Suspension>
<Primary Culture>

The SC21 strain yeast cells for use in culture for trial production were prepared as follows.

(1) The YPD medium (1.5 L) was put into each of four 5-L flasks.
(2) The YPD medium was autoclaved (121° C., 15 minutes).
(3) The *Saccharomyces cerevisiae* SC21 strain was inoculated into the autoclaved YPD medium, and cultured under the following conditions.
Culture temperature: 30° C.
Shaking: 200 rpm (rotary shaker)
Culture time: 24 hours
<Secondary Culture>
A starting medium having the following composition was prepared through heat sterilization at 120° C. for 20 minutes.
(Starting Medium)

| | |
|---|---|
| Glucose | 5 kg |
| Phosphoric acid | 270 ml |
| Magnesium sulfate heptahydrate | 585 g |
| Yeast extract | 2.7 kg |
| Reverse osmosis membrane-treated water | 85 L |

(Culture Conditions)
Inoculation amount: 6 L of Primary culture liquid
Culture temperature: 32° C.
Aeration: 200 L/minute
Stirring: Not performed
pH at the start of culture: pH 6.0 (adjusted with sodium hydroxide)
Culture time: 16 hours
<Tertiary Culture>
A starting medium having the following composition was prepared through heat sterilization at 120° C. for 20 minutes.
(Starting Medium)

| | |
|---|---|
| Urea | 1.2 kg |
| Phosphoric acid | 160 ml |
| Magnesium sulfate heptahydrate | 30 g |
| Yeast extract | 2.7 kg |
| Reverse osmosis membrane-treated water | 220 L |

(Culture Conditions)
Inoculation amount: 90 L of secondary culture liquid
Culture temperature: 32° C.
Aeration: 1.2 kL/minute
Stirring: 400 rpm
pH Control: 4.5 as the lowest pH (adjusted by addition of 15% sodium carbonate)
Feed medium: Molasses (sugar content, 43%); volume, 80 L (added portionwise in appropriate volumes so that growth inhibition was not caused)
Culture time: 16 hours
<Quaternary Culture>
A starting medium having the following composition was prepared through heat sterilization at 120° C. for 20 minutes.
(Starting Medium)

| | |
|---|---|
| Urea | 23 kg |
| Phosphoric acid | 3.2 L |
| Magnesium sulfate heptahydrate | 585 g |
| Yeast extract | 2.1 kg |
| Reverse osmosis membrane-treated water | 2200 L |

(Culture Conditions)
Inoculation amount: 310 L of tertiary culture liquid
Culture temperature: 32° C.
Aeration: 5 kL/minute
Stirring: 400 rpm
pH Control: 4.5 as the lowest pH (adjusted by addition of 15% sodium carbonate)
Feed medium: Molasses (sugar content, 43%); volume, 100 L (added portionwise in appropriate volumes so that growth inhibition was not caused)
Culture time: 16 hours
After the aforementioned quaternary culture, the yeast cells were separated with a nozzle separator, and washed with clean water, and then a suspension of the yeast cells was prepared. The obtained yeast suspension was used for the following main culture.
<Main Culture>
(Composition of Starting Medium)

| | |
|---|---|
| Urea | 43 kg |
| Phosphoric acid | 6.5 L |
| Magnesium sulfate heptahydrate | 1 kg |
| Yeast extract | 4.2 kg |

A total volume of 2600 L was obtained by adding reverse osmosis (RO)-treated water.
(Culture conditions)
Yeast suspension: 80 L
Culture temperature: 32° C.
Aeration: 5 kL/minute
Stirring: 400 rpm
KLa: 350 to 450 $hr^{-1}$ at the end of culture
pH Control: 4.5 as the lowest pH (adjusted by addition of 15% sodium carbonate) Feed medium: Molasses (sugar content, 43%); volume, 1000 L (added portionwise in appropriate volumes so that growth inhibition was not caused)
Culture time: 15 hours
<Organic Acid Generation Treatment Conditions>
The yeast cells collected from the culture liquid were washed, water was added to the cells to obtain a yeast cell suspension containing 170 g/L of the yeast cells in terms of dry yeast cell weight, and the yeast suspension was subjected to the organic acid generation treatment performed under the following conditions.
Temperature: 46° C.
pH: Controlled (pH 6.2 to 6.8)
Time: 6 Hours for trial productions 1, 2, and 4, or 9 hours for trial production 3
The yeast suspension was stirred at such a speed that the yeast suspension did not foam.
The dry yeast weight was obtained by weighing 5 g of yeast cell suspension on an aluminum dish of which tare weight was measured beforehand, drying the suspension at 105° C. for 6 hours in a drier, and measuring the weight after drying.
<Hot Water Treatment Conditions>
The yeast suspension was subjected to hot water extraction under the following conditions, and then insoluble ingredients were removed with a centrifugation machine.
Temperature: 85° C.
Time: 30 minutes
Stirring: Stirring at such a rate that the yeast suspension did not get burned on the internal surface of the container.

<Filtration Conditions>

The yeast extract obtained after the removal of the insoluble ingredients was filtered through a precision filtration membrane.
Filtration membrane: Microza USW543 (Asahi Kasei Chemicals)
<Concentration Conditions>

The filtered yeast extract was concentrated in a vacuum concentration machine.
Internal temperature: 50° C.
Solid content at the end of concentration: 43.9%

The results are shown in the following table. In the table, the indication "treatment" means the organic acid generation treatment. The indication "extract" means the yeast extract finally obtained through the hot water treatment, filtration treatment, and concentration treatment after the organic acid generation treatment. In the table, the values of the intracellular nitrogen at the end of the culture are percentages based on the dry weight of the yeast cells (%/dry yeast weight). The values of the amounts of ingredients before and after the treatment are percentages based on dry weight of the yeast cells (%/dry yeast weight), and the values of the amounts of ingredients in extract are percentages based on dry weight of yeast extract (%/dry yeast extract weight).

added in an amount of 50 to 60% of the dry cell weight to prepare a yeast cell suspension. The yeast cell suspension (160 g) was put into each of three tall beakers. Under three kinds of the conditions shown in the following table, the organic acid generation treatment or autolysis treatment (conditions 1 or conditions 2) was performed, samples were taken over time, and precipitation volume (packed volume, PV) was measured. The method of the organic acid generation treatment was the same as that of Example 9, and the autolysis treatments under the conditions 1 and 2 were performed by maintaining the cell suspension at an autolysis temperature of 40° C. or 52° C. without controlling pH according to the method of Patent document 9 (WO2012/067106) mentioned above, Example 9.

The packed volume (PV) was measured as follows.

The yeast suspension (10 ml) was put into a spitz tube, and centrifuged at 3,000 rpm for 15 minutes, and then PV was confirmed. PV is indicated as a relative value of the value read from the scale of the spitz tube based on 10 ml, which was taken as 100. For example, PV of 70 means that precipitations of 7.0 ml were observed.

TABLE 18

| | Trial production 1 | | | Trial production 2 | | | Trial production 3 | | | Trial production 4 | | |
|---|---|---|---|---|---|---|---|---|---|---|---|---|
| | Intracellular nitrogen at the end of culture | | | | | | | | | | | |
| | 8.1 | | | 7.8 | | | 8.3 | | | 7.9 | | |
| | Before treatment | After treatment | Extract | Before treatment | After treatment | Extract | Before treatment | After treatment | Extract | Before treatment | After treatment | Extract |
| Citric acid | 0.8 | 0.4 | 1.2 | 0.8 | 0.6 | 1.6 | 0.8 | 0.3 | 1.0 | 1.0 | 0.7 | 2.0 |
| Malic acid | 0.3 | 0.1 | 0.2 | 0.1 | 0.1 | 0.4 | 0.2 | 0.1 | 0.2 | 0.2 | 0.1 | 0.2 |
| Succinic acid | 0.6 | 2.8 | 9.7 | 0.6 | 3.0 | 10.2 | 0.5 | 3.4 | 11.9 | 0.4 | 2.9 | 9.8 |
| Lactic acid | 0.1 | 0.3 | 1.1 | 0.1 | 0.4 | 1.4 | 0.2 | 0.3 | 1.0 | 0.1 | 0.9 | 3.2 |
| Acetic acid | 0.1 | 0.9 | 2.9 | 0.1 | 0.5 | 1.5 | 0.1 | 1.1 | 3.5 | 0.1 | 0.7 | 2.2 |
| Pyroglutamic acid | 0.6 | 0.5 | 2.3 | 0.6 | 0.4 | 2.1 | 1.0 | 0.6 | 2.6 | 0.8 | 0.5 | 2.8 |
| Asp | 0.2 | 0.1 | 0.4 | 0.5 | 0.2 | 0.8 | 0.1 | 0.0 | 0.3 | 0.5 | 0.2 | 0.8 |
| Thr | 1.1 | 0.4 | 0.3 | 0.8 | 0.5 | 0.7 | 1.1 | 0.5 | 0.7 | 1.0 | 0.4 | 0.7 |
| Ser | 0.2 | 0.0 | 0.1 | 0.2 | 0.1 | 0.3 | 0.1 | 0.0 | 0.1 | 0.2 | 0.1 | 0.3 |
| Glu | 4.2 | 5.4 | 19.2 | 3.6 | 4.5 | 15.6 | 4.2 | 5.4 | 19.0 | 3.4 | 4.3 | 14.5 |
| Gly | 0.2 | 0.3 | 1.1 | 0.3 | 0.3 | 1.2 | 0.2 | 0.3 | 1.2 | 0.3 | 0.3 | 1.2 |
| Ala | 0.8 | 0.9 | 3.1 | 0.8 | 0.9 | 3.3 | 0.9 | 1.0 | 3.6 | 0.9 | 1.0 | 3.3 |
| Cys | 0.2 | 0.2 | 0.5 | 0.1 | 0.2 | 0.2 | 0.2 | 0.2 | 0.5 | 0.1 | 0.1 | 0.2 |
| Val | 0.2 | 0.2 | 0.8 | 0.2 | 0.2 | 0.8 | 0.2 | 0.2 | 0.9 | 0.2 | 0.2 | 0.7 |
| Met | 0.0 | 0.0 | 0.1 | 0.0 | 0.0 | 0.1 | 0.0 | 0.0 | 0.1 | 0.0 | 0.0 | 0.1 |
| Ile | 0.2 | 0.2 | 0.6 | 0.2 | 0.2 | 0.7 | 0.2 | 0.2 | 0.6 | 0.2 | 0.2 | 0.6 |
| Leu | 0.1 | 0.1 | 0.4 | 0.1 | 0.1 | 0.3 | 0.1 | 0.1 | 0.4 | 0.1 | 0.1 | 0.3 |
| Tyr | 0.1 | 0.1 | 0.1 | 0.1 | 0.1 | 0.1 | 0.1 | 0.1 | 0.1 | 0.1 | 0.0 | 0.1 |
| Phe | 0.1 | 0.2 | 0.3 | 0.2 | 0.2 | 0.3 | 0.2 | 0.2 | 0.3 | 0.2 | 0.2 | 0.3 |
| Lys | 0.1 | 0.1 | 0.4 | 0.1 | 0.2 | 0.4 | 0.2 | 0.2 | 0.4 | 0.1 | 0.2 | 0.3 |
| His | 0.1 | 0.1 | 0.3 | 0.1 | 0.2 | 0.2 | 0.2 | 0.2 | 0.3 | 0.2 | 0.2 | 0.2 |
| Arg | 0.5 | 0.4 | 1.1 | 0.6 | 0.5 | 1.7 | 0.5 | 0.4 | 1.5 | 0.7 | 0.6 | 1.7 |
| Pro | 0.7 | 0.1 | 2.2 | 0.8 | 0.7 | 2.5 | 0.6 | 0.6 | 2.2 | 0.8 | 0.7 | 2.1 |
| Total | 8.7 | 8.8 | 31.1 | 8.6 | 9.1 | 29.3 | 9.1 | 9.8 | 32.2 | 8.7 | 8.6 | 27.4 |

Succinic acid was increased by the organic acid generation treatment as in the investigations in a laboratory scale described above.

Reference Example: Comparison with Autolysis Treatment

Cells of the *Saccharomyces cerevisiae* SC21 strain were collected, and washed. To the cells, distilled water was The results are shown in the following table. With the organic acid generation treatment, PV was not decreased, and thus it was estimated that the cells were maintained, and collapse of the structures by autolysis did not occur, at least. On the other hand, with the autolysis treatment, PV was decreased, and thus it was estimated that collapse of the yeast cell structures was caused by reactions catalyzed by enzymes in the yeast cells.

TABLE 19

| | Conditions | | PV | | | |
|---|---|---|---|---|---|---|
| | Temperature | pH Adjustment | 0 h | 8 h | 20 h | 32 h |
| Organic acid generation treatment | 47 | 6.8 | 70 | 69 | 67 | 70 |
| Autolysis treatment (Conditions 1) | 40 | None | 70 | 70 | 60 | 59 |
| Autolysis treatment (Conditions 2) | 52 | None | 70 | 69 | 38 | 38 |

On the basis of the above results, it is considered that the cell structures collapsed under the conditions of Patent document 9 (WO2012/067106), and specific enzymes exist in free forms, and catalyze the reactions. On the other hand, it seems that, in the organic acid generation treatment of the present invention, succinic acid is produced under such conditions that collapse of the structures of yeast cells does not occur, and enzymes involved in various metabolic systems remaining in the maintained yeast cell structures exist in a state that they are captured in the structures. Therefore, it is considered that, according to the method of Patent document 9, the enzymes disorderly function, and thus a specific useful ingredient (for example, succinic acid) can be obtained only under quite special conditions (low volumetric oxygen transfer rate conditions), or the like, but according to the present invention, the enzymes remain in a state that the original orders of yeast cells are maintained, and therefore there are established such conditions that they can increase a specific ingredient under relatively mild conditions, and in such a case, another useful ingredient that is originally easily decomposed (for example, useful amino acids such as glutamic acid) can be remained. Therefore, it is considered that the process is a process different from the conventional autolysis treatment step.

INDUSTRIAL APPLICABILITY

The present invention is useful in the field of food manufacturing, and so forth. The present invention provides a method for producing a yeast extract containing an organic acid at a high concentration. According to a preferred embodiment, the present invention provides a method for producing a yeast extract that contains both succinic acid and glutamic acid at high concentrations, and the obtained yeast extract that contains succinic acid and glutamic acid at high concentrations can improve seafood flavor in foods, and can enhance taste by synergistic effect of succinic acid and glutamic acid. The method for producing a yeast extract provided by the present invention enables commercial production of a yeast extract containing succinic acid and glutamic acid at high concentrations.

The invention claimed is:

1. A method for producing a yeast extract, the method comprises:
    maintaining a suspension of cultured yeast that belongs to the genus *Saccharomyces* or *Candida* for 2 to 30 hours at 40 to 55° C. and pH 4.0 to 7.5 to increase succinic acid content in the yeast; and
    extracting a yeast extract from the yeast with hot water to obtain the yeast extract that contains 5.0% by weight or more of succinic acid based on dry weight of the yeast extract in case that the yeast belongs to the genus *Saccharomyces* or the yeast extract that contains 2.0% by weight or more of succinic acid based on dry weight of the yeast extract in case that the yeast belongs to the genus *Candida*,
    wherein the cultured yeast to be subjected to the step of maintaining has been cultured under such conditions that the volumetric oxygen transfer rate (KLa) is 300 $hr^{-1}$ or higher.

2. The method according to claim 1, wherein the hot water is at 56° C. or higher.

3. The method according to claim 1, wherein amount of nitrogen contained in the cultured yeast to be subjected to the step of maintaining is 8.5% or lower based on dry weight of the yeast.

4. The method according to claim 1, wherein the conditions of the step of maintaining also increase glutamic acid content of the yeast.

5. The method according to claim 1, wherein the yeast is a glutamic acid-rich yeast strain.

6. A yeast extract produced by the method according to claim 1, wherein:
    in case that the yeast belongs to the genus *Saccharomyces*, the obtained yeast extract contains 10.0% by weight or more of glutamic acid based on dry weight of the yeast extract, or
    in case that the yeast belongs to the genus *Candida*, the obtained yeast extract contains 6.0% by weight or more of glutamic acid based on dry weight of the yeast extract.

* * * * *